(12) United States Patent
Imanishi et al.

(10) Patent No.: US 10,024,832 B2
(45) Date of Patent: Jul. 17, 2018

(54) METHOD FOR EVALUATING VITALITY OF PLANT, AND MEASUREMENT SYSTEM AND EVALUATION SYSTEM

(71) Applicants: Kyoto University, Kyoto-shi, Kyoto (JP); HAMAMATSU PHOTONICS K.K., Hamamatsu-shi, Shizuoka (JP)

(72) Inventors: Junichi Imanishi, Kyoto (JP); Masakazu Katsumata, Hamamatsu (JP); Yuko Kobayashi, Hamamatsu (JP)

(73) Assignees: KYOTO UNIVERSITY, Kyoto-shi, Kyoto (JP); HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 244 days.

(21) Appl. No.: 14/277,209

(22) Filed: May 14, 2014

(65) Prior Publication Data

US 2014/0343863 A1 Nov. 20, 2014

(30) Foreign Application Priority Data

May 17, 2013 (JP) ................................. 2013-105085

(51) Int. Cl.
*G01N 33/00* (2006.01)
*G01N 21/64* (2006.01)
*G01N 21/63* (2006.01)

(52) U.S. Cl.
CPC ..... *G01N 33/0098* (2013.01); *G01N 21/6408* (2013.01); *G01N 2021/635* (2013.01); *G01N 2021/6484* (2013.01); *G01N 2201/0221* (2013.01)

(58) Field of Classification Search
None
See application file for complete search history.

(56) References Cited

U.S. PATENT DOCUMENTS

| 6,402,986 B1 | 6/2002 | Jones, II et al. |
| 2011/0182825 A1 | 7/2011 | Mik |

FOREIGN PATENT DOCUMENTS

| JP | 2000-002659 | 1/2000 |
| JP | 2000214089 | 8/2000 |
| JP | 2005-308733 | 11/2005 |
| JP | 2005-326241 | 11/2005 |
| WO | WO 2007/097341 | 8/2007 |

OTHER PUBLICATIONS

Yan et al. J. Photochemistry Photobiology, 78, 235-244, 2005.*
Havaux et al. Trends in Plant Science vol. 11 No. 10, 480-484.*
Chaerle et al. Biochimica et Biophysica Acta 1519, 2001,153-166.*
Imanishi, J., et al., Kyoto Sango University, Motoyama, Kamigamo, Kita-Ku, Kyoto, Japan, "The 53rd Annual Meeting of the Japanese Society of Plant Physiology," "The Change of the Delayed Fluorescence Curve Depending on the Stress Condition of a Tree," Mar. 2012, p. 255 (with attached at least partial English-language translation).
Imanishi, J., et al., Kyoto University, School of Global Environmental Studies, Hamamatsu Photonics, K.K., Central Research Lab, "The Change of the Delayed Fluorescence Curve Depending on the Stress Condition of a Tree," Mar. 2012 (with attached at least partial English-language translation).

* cited by examiner

*Primary Examiner* — Michael Borin
(74) *Attorney, Agent, or Firm* — Drinker Biddle & Reath LLP

(57) ABSTRACT

The present invention discloses a method for evaluating vitality of a plant including (a) a step of measuring a delayed luminescence of a leaf of each plant of a group of plants subject to evaluation to obtain data of delayed luminescence amount, and (b) a step of processing data of a plurality of delayed luminescence amounts thus obtained to evaluate a plant exhibiting a delayed luminescence amount not less than a preset upper limit threshold as an individual of poor growth or evaluate a plant exhibiting a delayed luminescence amount not more than a preset lower limit threshold as an individual of good growth, and a measurement system and an evaluation system used for the method.

3 Claims, 21 Drawing Sheets

(a)

(b)

(a)

(b)

(a)

(b)

(c)

(a)

(b)

(c)

(d)

(a)

(b)

(c)

(a)

(b)

METHOD FOR EVALUATING VITALITY OF PLANT, AND MEASUREMENT SYSTEM AND EVALUATION SYSTEM

CROSS REFERENCE TO RELATED APPLICATIONS

This application claims priority to Japanese Patent Application No. 2013-105085 filed on May 17, 2013, which is hereby incorporated by reference in its entirety.

BACKGROUND OF THE INVENTION

Field of the Invention

The present invention relates to a method for evaluating vitality of a plant, and a measurement system and an evaluation system that are used in this method.

Related Background Art

Evaluation of growth states of agricultural plants, such as trees, shrubs, horticultural plants, vegetables, etc., for early determination of an anomaly, such as a pathological change, senescence, or withering, etc., or production of agricultural products of high added value (such as, tomatoes with high sugar content) by cultivation by loading of a suitable degree of stress is becoming an important theme for environmental conservation, agriculture, agricultural product processing industry, etc.

As a conventional method of evaluating the growth states of such plants, a subjective method of visual observation, etc., based on experience is generally used. However, realization of a method of evaluation of growth states based on objective indices is desired.

For example, in Patent Literature 1 is described a method for measuring stress received by a plant by irradiating light on a green leaf of the plant and capturing the reflected light or transmitted light from the green leaf to make multiple measurements with time of spectral ratio characteristics of spectral ratios obtained by dividing spectral luminances of respective wavelengths of the reflected light or transmitted light by spectral luminances of the same wavelengths of reflected light or transmitted light from an object serving as a reference for the irradiated light, detecting, for the respective spectral ratio characteristics, a change wavelength range in which the spectral ratio changes greatly from a low spectral ratio in a red visible light range to a high spectral ratio in a near-infrared range, determining the variation with time of the change wavelength range, and evaluating that the stress received by the plant is greater when the transition toward the short wavelength side in the variation of the change wavelength range is greater.

Also, in Patent Literature 2 is described a method for evaluating environmental stress tolerability of a plant that includes evaluation of photostress tolerance of the plant by intermittently irradiating a photosynthetic organ of the plant with saturation light pulses under the absence of photosynthesis light to measure the level of photoinhibition of photosynthesis caused thereby.

Further, in Non-Patent Literature 1 and Non-Patent Literature 2 is described an observation of how a pattern of a delayed luminescence curve of a leaf changes according to difference in stress state of a tree, and it is described that a control group and a drought stress group can be identified by plotting a second corrected delayed luminescence amount, obtained by correction by chlorophyll amount per predetermined leaf area of a second delayed luminescence amount, which is a delayed luminescence amount corresponding to a time domain in which the delayed luminescence amount decreases when xylem pressure potential is decreased, against a first corrected delayed luminescence amount, obtained by correction by the chlorophyll amount per predetermined leaf area of a first delayed luminescence amount, which is a delayed luminescence amount corresponding to a time domain in which the delayed luminescence amount increases when the xylem pressure potential is decreased.

PRIOR ART DOCUMENTS

Patent Literatures

[Patent Literature 1] Japanese Patent Application Laid-Open No. 2005-308733
[Patent Literature 2] Japanese Patent Application Laid-Open No. 2005-326241

Non-Patent Literatures

[Non-Patent Literature 1] Abstracts of the 53rd Annual Meeting of the Japanese Society of Plant Physiologists (March, 2012), p. 255.
[Non-Patent Literature 2] Poster Presentation in the 53rd Annual Meeting of the Japanese Society of Plant Physiologists (March, 2012), PF025 (0489).

SUMMARY OF THE INVENTION

Problems to be Solved by the Invention

To perform growth evaluation of an agricultural plant, such as a tree, shrub, horticultural plant, or vegetable, etc., in an outdoor setting for environmental conservation, agriculture, agricultural product processing industry, etc., a method and a measurement apparatus that enable the growth state of the plant to be evaluated simply, noninvasively, and accurately in a short time is required.

The methods described in Patent Literature 1 and Patent Literature 2 are methods respectively based on change of spectral ratio and on chlorophyll fluorescence. The change of spectral ratio is a phenomenon due to a change in chlorophyll concentration or leaf structure and is not an index that reflects the state of the photosynthesis system. Also, the chlorophyll fluorescence is fluorescence that is observed under excitation light and in comparison to delayed luminescence, only indirect information related to photosynthesis can be obtained. That is, delayed luminescence is a phenomenon in which weak luminescence arises from photosystem II as a result of a reverse reaction from the photosynthesis process and provides information that is more directly related to photosynthesis than the chlorophyll fluorescence observed under excitation light. The methods described in Patent Literature 1 and Patent Literature 2 thus cannot be said to be sufficient in accuracy.

On the other hand, although the method of Non-Patent Literatures 1 and 2 makes use of delayed fluorescence and is higher in accuracy, there is a need to measure and calculate the first and second corrected delayed luminescence amounts. There is thus room for improvement in terms of shortening the measurement time.

Therefore an object of the present invention is to provide a method for evaluating vitality of a plant simply, noninvasively, and accurately in a short time, it is also an object of the present invention to provide a measurement system and a vitality evaluation system used in the method for evaluating vitality.

Means for Solving the Problem(s)

The present inventors found, in regard to the delayed luminescence pattern of a plant leaf, that whereas the second delayed luminescence amount that is the delayed luminescence amount corresponding to the time domain in which the delayed luminescence amount decreases when the xylem pressure potential is decreased differs largely among individual plants, the first delayed luminescence amount that is the delayed luminescence amount corresponding to the time domain in which the delayed luminescence amount increases when the xylem pressure potential is decreased is comparatively small in difference among individual plants, and thus the correlation between the delayed luminescence amount and the degree of drought stress can be high. The present inventors arrived at the present invention based on these findings.

That is, the present invention provides a method for evaluating vitality of a plant including (a) a step of measuring, for each plant of a group of plants subject to evaluation, a delayed luminescence of a leaf to obtain data of delayed luminescence amount in a time domain in which the delayed luminescence amount increases when xylem pressure potential is decreased, and (b) a step of processing data of a plurality of delayed luminescence amounts thus obtained to evaluate a plant exhibiting a delayed luminescence amount not less than a preset upper limit threshold as an individual of poor growth or evaluate a plant exhibiting a delayed luminescence amount not more than a preset lower limit threshold as an individual of good growth.

The above method for evaluating vitality is a method in which the growth state of a plant is evaluated based on the specific delayed luminescence amount and therefore enables vitality evaluation to be performed simply, noninvasively, and accurately in a short time. In particular, by the method for evaluating vitality according to the present invention, the growth state of the plant can be judged by the delayed luminescence at an initial stage of measurement, thus enabling a large amount of samples to be processed in a short time and being significant in measurement time reduction effect in comparison to the conventional methods.

The present inventors further found that in the time domain in which the delayed luminescence amount increases when the xylem pressure potential is decreased, there is present a time domain in which a correlation between the delayed luminescence amount and the degree of drought stress is significantly high in comparison to correlation between chlorophyll fluorescence (Fv/Fm), which is known as a general index that reflects the photosynthesis activity state, and the degree of drought stress. Vitality evaluation at a higher accuracy than conventional methods is thus made possible by measuring the data of delayed luminescence amount in this time domain.

With the method for evaluating vitality, the data of delayed luminescence amount are preferably data included in a time domain of 0.01 seconds to 5 seconds after excitation light irradiation. Evaluation of higher accuracy is enabled by use of the delayed luminescence amount data in this range.

The method for evaluating vitality may further comprises (c) a step of measuring a chlorophyll amount in the plant leaf to obtain chlorophyll amount data and (d) a step of calculating data of corrected delayed luminescence amount by correcting the data of delayed luminescence amount obtained in step (a) by the chlorophyll amount per predetermined area, and the data of corrected delayed luminescence amount may be used in place of the data of delayed luminescence amount in step (b). Evaluation at even higher accuracy is made possible by correcting by the chlorophyll amount.

Also in another mode, the present inventors found that in the delayed luminescence pattern of a plant leaf, the delayed luminescence amount in a predetermined time domain has a high correlation with the degree of stress.

That is, the present invention provides a method for evaluating vitality of a plant comprising (a') a step of measuring a delayed luminescence of a leaf of each plant of a group of plants subject to evaluation to obtain data of delayed luminescence amount in a time domain of 10 to 50 seconds after excitation light irradiation, and (b') a step of processing data of a plurality of delayed luminescence amounts thus obtained to evaluate a plant exhibiting a delayed luminescence amount not less than a preset upper limit threshold as an individual of good growth or evaluate a plant exhibiting a delayed luminescence amount not more than a preset lower limit threshold as an individual of poor growth.

The above method for evaluating vitality is a method in which the growth state of a plant is evaluated based on the specific delayed luminescence amounts and therefore enables vitality evaluation of the plant to be performed simply, noninvasively, and accurately in a short time.

The data of delayed luminescence amount are preferably data in a time domain in which the absolute value of a correlation coefficient of leaf water potential (the xylem pressure potential may be regarded to be the water potential because osmotic potential is close to zero) or terminal branch growth increment and the delayed luminescence amount is greater than the absolute value of a correlation coefficient of the leaf water potential or terminal branch growth increment and the chlorophyll fluorescence (Fv/Fm).

The data processing in step (b) or (b') of the method for evaluating vitality may be performed by any of the following (i), (ii), and (iii).

(i) Ranking the data based on the delayed luminescence amount.

(ii) Assuming a normal distribution to calculate a prediction interval corresponding to the preset upper limit threshold or lower limit threshold and classifying the data based on the prediction interval.

(iii) Calculating, by a bootstrap method, a confidence interval of percentile value corresponding to the preset upper limit threshold or lower limit threshold and classifying the data based on the confidence interval.

With (i), a predetermined number of individual plants can be selected and the method is thus advantageous in a case where a predetermined number of individual plants of good growth or poor growth is to be selected. With (ii) and (iii), the advantages that the variation of data is also taken into consideration and characterization of the growth state of the plant group can be performed at the same time are provided. The data processing may be performed by any one of (i), (ii), and (iii) or a combination of any two of the methods or a combination of the three methods may be used.

The present invention also provides a method for evaluating vitality of a plant comprising a step of measuring delayed luminescence amounts of a leaf of a plant subject to evaluation at x seconds and y seconds after excitation light irradiation (where, x and y are positive real numbers and x≠y) to obtain two data items $D_{x1}$ and $D_{x2}$ of delayed luminescence amount, a step of obtaining an operated value by any of the following formulae (1), (2), and (3) using $D_{x1}$ and $D_{x2}$, and a step of evaluating a vitality state of the plant by comparing the operated value thus obtained and a predetermined threshold.

$$O=D_{x1}/D_{x2} \quad (1)$$

$$O=D_{x1}-D_{x2} \quad (2)$$

$$O=(D_{x1}-D_{x2})/(D_{x1}+D_{x2}) \quad (3)$$

[In the formulae (1), (2), and (3), $D_{x1}$ represents the data item of delayed luminescence amount at x seconds after excitation light irradiation, $D_{x2}$ represents the data item of delayed luminescence amount at y seconds after excitation light irradiation, and O represents the operated value.]

The above method for evaluating vitality is a method in which the vitality/growth state of a plant is evaluated based on the specific delayed luminescence amounts and therefore enables vitality evaluation of the plant to be performed simply, noninvasively, and accurately in a short time. Also, an effect of reducing influence of error due to differences in measuring equipment and of measurement noise is exhibited by the use of the operated value that expresses a relationship between the two delayed luminescence amount data items. Also, in a case where the calculated value is obtained by (1) or (3) above, an effect of reducing influence of chlorophyll concentration that differs according to sample is provided to enable evaluation at even higher accuracy.

Preferably in the method for evaluating vitality, x and y are included in a time domain of 0.2 to 300 seconds after excitation light irradiation. The correlation of the calculated value obtained by using the delayed luminescence amount data items in this time domain and a vitality index is especially high and evaluation at even higher accuracy is thus enabled.

The present invention also provides a method for evaluating vitality of a plant comprising a step of measuring a delayed luminescence amount of a leaf of a plant subject to evaluation at a plurality of points in a preset time domain to obtain a plurality of data items of delayed luminescence amount, a step of approximating a relationship between elapsed time X after excitation light irradiation and the corresponding delayed luminescence amount Y by a curve approximation formula using the plurality of delayed luminescence amount data items to obtain at least one value selected from the group consisting of constants in the approximation formula, as a coefficient value, and a step of evaluating a vitality state of the plant by comparing the coefficient value thus obtained and a predetermined threshold.

The above method for evaluating vitality is a method in which the growth state of a plant is evaluated based on the specific delayed luminescence amounts and therefore enables vitality evaluation of the plant to be performed simply, noninvasively, and accurately in a short time. Also, an effect of reducing influence of error due to differences in measuring equipment and of measurement noise is exhibited by the use of the coefficient value obtained by using the delayed luminescence amount data items at the plurality of points in the time domain.

As the coefficient value, one or more values selected from the group consisting of a, b, c, d, e, and $\lambda$ in the following formulae (4), (5), and (6) may be used.

$$Y=a \cdot b^X \quad (4)$$

$$Y=a \cdot e^{(-\lambda \cdot X)} \quad (5)$$

$$Y=c+d \cdot X+e \cdot X^2 \quad (6)$$

[In the formulae (4), (5), and (6), X and Y are the elapsed time X after excitation light irradiation in the preset time domain and the corresponding delayed luminescence amount Y.]

By use of the coefficient value, evaluation at higher accuracy is enabled. Also, in a case where the b or $\lambda$ is used as the coefficient value, an effect of reducing influence of chlorophyll concentration that differs according to sample is provided to enable evaluation at even higher accuracy.

Preferably in the method for evaluating vitality, the time domain is included within a range of 0.1 to 300 seconds after excitation light irradiation. With the delayed luminescence amount data items in the time domain in this range, the correlation of the coefficient value obtained and the vitality index is especially high and evaluation at even higher accuracy is thus enabled.

The data may be processed in the evaluating step by any of the following (i), (ii), and (iii).

(i) Ranking the data based on the operated value or the coefficient value obtained.

(ii) Assuming a normal distribution to calculate a prediction interval corresponding to a preset upper limit threshold or lower limit threshold and classifying the data based on the prediction interval.

(iii) Calculating, by a bootstrap method, a confidence interval of percentile value corresponding to the preset upper limit threshold or lower limit threshold and classifying the data based on the confidence interval.

The method for evaluating vitality may further comprise a step of measuring a chlorophyll amount in the plant leaf to obtain chlorophyll amount data and a step of calculating data of corrected delayed luminescence amount by correcting the obtained data of delayed luminescence amount by the chlorophyll amount per predetermined area, and the data items of corrected delayed luminescence amount may be used in place of the data items of delayed luminescence amount in the step of obtaining the processing result. Evaluation at even higher accuracy is made possible by correcting by the chlorophyll amount.

Preferably in the method for evaluating vitality, the vitality reflects an influence of acute stress or chronic stress.

The present invention also provides a measurement system for evaluating vitality of a plant comprising a dark treatment tool, arranged to shade a portion or all of a leaf of a plant and having an opening capable of being opened and closed, and a measurement apparatus, having a light collecting unit capable of being attached to and detached from the opening, a light source unit arranged to irradiate light onto the plant leaf, and a delayed luminescence detecting unit detecting delayed luminescence of the plant leaf resulting from the light irradiated by the light source unit.

With the measurement system according to the present invention, vitality evaluation of the plant can be performed simply, noninvasively, and accurately in a short time by adoption of the arrangement described above. In particular, by being provided with the dark treatment tool, a dark treatment can be performed on all or a portion of an individual leaf of a tree without cutting the individual leaf, thereby enabling improvement of judgment accuracy and reduction of measurement time. The measurement system according to the present invention is used favorably in a vitality evaluation system according to the present invention.

The measurement system preferably includes a plurality of the dark treatment tools.

By being provided with a plurality of the dark treatment tools, it becomes possible to perform the dark treatment on a plurality of leaves in advance to enable measurements of dark-treated individual leaves to be made at any time and the measurement time is thereby shortened significantly.

The measurement apparatus may further comprise a photodetecting unit detecting light that arises as a result of the light irradiated by the light source unit and reflects the chlorophyll amount in the plant leaf, and a recording unit recording data of delayed luminescence amount corresponding to the delayed luminescence detected by the delayed luminescence detecting unit and chlorophyll amount data corresponding to the light, reflecting the chlorophyll amount, detected by the photodetecting unit.

Correction by the chlorophyll amount is thereby enabled.

The present invention also provides a plant vitality evaluation system comprising an acquisition means acquiring delayed luminescence amount data of a leaf of a plant, an operation means calculating an index value by processing the acquired delayed luminescence amount data, an evaluation means evaluate vitality of the plant by comparing the index value and a predetermined threshold, and a display means displaying the evaluation result to a user, and the operation means calculates, as the index value, a value obtained by one or more operating methods selected from the group consisting of the following (A), (B), and (C).

(A) A method using, as the index value, a value of the delayed luminescence amount at the time when a fixed preset time elapsed after excitation light irradiation.

(B) A method using, as the index value, a value represented by any of the following (1), (2), and (3).

$$D_{x1}/D_{x2} \quad (1)$$

$$D_{x1}-D_{x2} \quad (2)$$

$$(D_{x1}-D_{x2})/(D_{x1}+D_{x2}) \quad (3)$$

[In the formulae (1), (2), and (3), $D_{x1}$ represents the delayed luminescence amount at x seconds after excitation light irradiation and $D_{x2}$ represents the delayed luminescence amount at y seconds after excitation light irradiation. Here, x and y are positive real numbers and x≠y.]

(C) A method using, as the index value, at least one value selected from the group consisting of constants in a curve approximation formula approximating a relationship between elapsed time X after excitation light irradiation and the corresponding delayed luminescence amount Y.

By having such an arrangement, the vitality evaluation system according to the present invention enables vitality evaluation of the plant to be performed simply, noninvasively, and accurately in a short time.

As the index value in (C) above, one or more values selected from the group consisting of a, b, c, d, e, and λ in the following formulae (4), (5), and (6) may be used.

$$Y=a \cdot b^X \quad (4)$$

$$Y=a \cdot e^{(-\lambda \cdot X)} \quad (5)$$

$$Y=c+d \cdot X+e \cdot X^2 \quad (6)$$

[In the formulae (4), (5), and (6), X and Y are the elapsed time X after excitation light irradiation in the preset time domain and the corresponding delayed luminescence amount Y.]

In the vitality evaluation system, the threshold may be set in advance.

The vitality evaluation system may further comprise an input means inputting a vitality index of the plant, the operation means may further calculate correlation coefficients of index values calculated by two or more of the operation methods selected from the group consisting of (A), (B), and (C) above and the input vitality index and determine the operation method that exhibits the highest correlation coefficient, and the display means may further display the operation method to the user.

By the vitality evaluation system having such an arrangement, the evaluation can be performed more simply and more accurately.

In the vitality evaluation system, the vitality index is preferably a water potential (xylem pressure potential), a branch growth increment, a trunk growth increment, or a vitality evaluation rank according to expert (a value that quantitatively expresses a result of vitality evaluation by expert).

The vitality evaluation system may further comprise the measurement system and a data transfer means outputting the delayed luminescence amount data obtained by the measurement system and inputting the delayed luminescence amount data into the acquisition means. By the evaluation system having such an arrangement, measurement of the delayed luminescence amount and vitality evaluation of the plant can be performed integrally.

Also, the vitality evaluation system may further comprise the measurement system and a data transfer means outputting the delayed luminescence amount data and the chlorophyll amount data obtained by the measurement system and inputting the delayed luminescence amount data and the chlorophyll amount data into the acquisition means, the operation means may calculate corrected delayed luminescence amount data by correcting the obtained delayed luminescence amount data by the chlorophyll amount per predetermined area and use the corrected delayed luminescence amount data in place of the delayed luminescence amount data.

Effect(s) of the Invention

The present invention provides a method that enables the vitality of a plant to be evaluated noninvasively and accurately in a short time. The present invention also provides a measurement system and a vitality evaluation system to be used in the method for evaluating vitality. The measurement system according to the present invention includes a dark treatment tool enabling a dark treatment to be performed on an individual leaf without cutting the leaf, thereby enabling measurement to be performed noninvasively and enabling improvement of judgment accuracy and reduction of measurement time. By the vitality evaluation system according to the present invention, vitality of a plant can be evaluated noninvasively and accurately in a short time.

In management of roadside trees, park trees, and garden trees, growth evaluation of the trees and shrubs is essential for growing the trees and shrubs healthily to improve the values thereof and for safety management for preventing toppling. Also in regard to horticultural plants, vegetables, and other agricultural plants, it is becoming an important theme to evaluate the growth states thereof to perform early determination of an anomaly, such as a pathological change, senescence, or withering, etc., or perform production of agricultural products of high added value (such as, high-sugar tomatoes) by cultivation by loading of a suitable degree of stress. However presently, the growth evaluation of such plants is determined based on experience in many cases. For example, in conservation of trees and shrubs by local governments, subjective judgments by investigators tend to give rise to differences according to the individual investigators and it is difficult to actively promote budgeting for conservation of precious trees and shrubs and roadside trees. It is predicted that much decline of trees and shrubs and anomaly of agricultural plants will occur due to global climate change, air pollution, and soil pollution. The method for evaluating vitality, the measurement system, and the vitality evaluation system according to the present invention, which enable selection of plants by enabling the growth state of a plant to be evaluated simply, noninvasively, and accurately in a short time, is thus anticipated to be useful.

DESCRIPTION OF THE PREFERRED EMBODIMENTS

Figure 1:
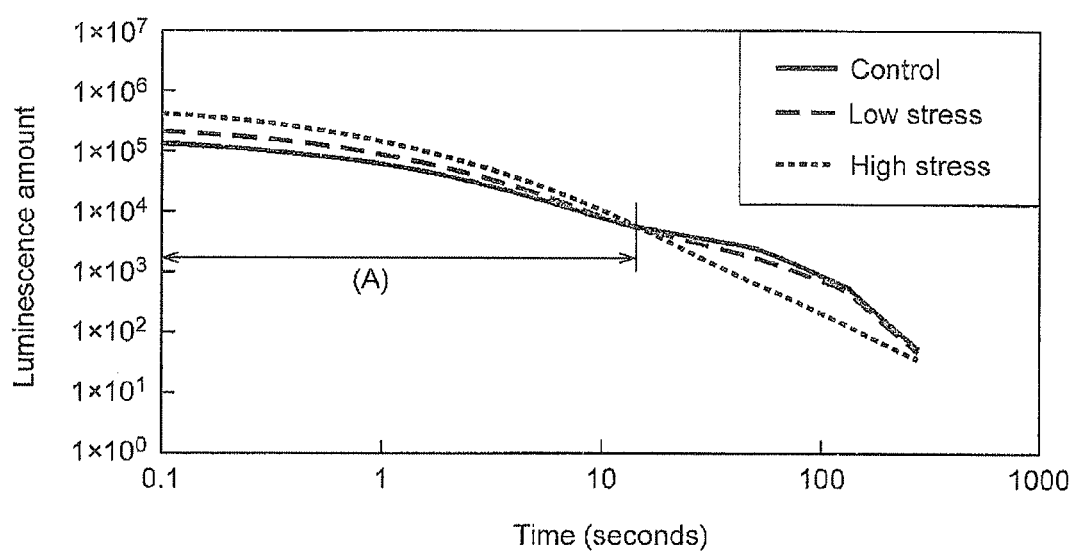
FIG. 1 is a graph of changes with time of delayed luminescence amounts of a control group and a stress group in Example 1 (Japanese mountain cherry).

Embodiments for carrying out the present invention shall now be described in detail. However, the present invention is not restricted to the embodiments described below.

A method for evaluating vitality of a plant according to a first embodiment of the present invention comprises (a) a step of measuring a delayed luminescence of a leaf of each plant of a group of plants subject to evaluation to obtain data of delayed luminescence amount in a time domain in which the delayed luminescence amount increases when xylem pressure potential is decreased, and (b) a step of processing data of a plurality of delayed luminescence amounts thus obtained to evaluate a plant exhibiting a delayed luminescence amount not less than a preset upper limit threshold as an individual of poor growth or evaluate a plant exhibiting a delayed luminescence amount not more than a preset lower limit threshold as an individual of good growth.

With the method for evaluating vitality of a plant according to the first embodiment, evaluation of vitality at even higher accuracy is made possible when the "preset thresholds" in the (b) step are thresholds set based on a vitality index that reflects acute stress. That is, the method for evaluating vitality of a plant according to the first embodiment may be a method for evaluating acute stress of a plant. As examples of acute stress, water stress accompanying a sudden variation of water potential (xylem pressure potential), drought stress, etc., can be cited.

A method for evaluating vitality of a plant according to a second embodiment of the present invention comprises (a') a step of measuring a delayed luminescence of a leaf of each plant of a group of plants subject to evaluation to obtain data of delayed luminescence amount in a time domain of 10 to 50 seconds after excitation light irradiation, and (b') a step of processing data of a plurality of delayed luminescence amounts thus obtained to evaluate a plant exhibiting a delayed luminescence amount not less than a preset upper limit threshold as an individual of good growth or evaluate a plant exhibiting a delayed luminescence amount not more than a preset lower limit threshold as an individual of poor growth.

With the method for evaluating vitality of a plant according to the second embodiment, evaluation of vitality at even higher accuracy is made possible when the "preset thresholds" in the (b') step are thresholds set based on a vitality index that reflects chronic stress. That is, the method for evaluating vitality of a plant according to the second embodiment may be a method for evaluating chronic stress of a plant. As examples of chronic stress, a branch growth increment, such as a terminal branch growth increment, etc., a trunk growth increment, a vitality evaluation rank according to expert, etc., can be cited.

<First Embodiment,(a) Step>

With the method for evaluating vitality according to the first embodiment of the present invention, in the (a) step of acquiring the data of the specific delayed luminescence amount, the delayed luminescence of a leaf is measured for each plant of a group of plants subject to evaluation to obtain the data of the delayed luminescence amount in the time domain in which the delayed luminescence amount increases when the xylem pressure potential is decreased.

As examples of the group of plants subject to evaluation, a group of plants growing in a certain region, a group of plants of the same species growing in a fixed growth environment, such as street trees planted at a predetermined interval, etc., can be cited.

In the first embodiment, the data of the delayed luminescence amount acquired in step (a) are data in the time domain in which the delayed luminescence amount increases when the xylem pressure potential is decreased (may also be referred to hereinafter as "time domain A"). For example, as shown in FIG. 1, in a case of a delayed luminescence pattern of a leaf of Japanese mountain cherry that is observed while changing the xylem pressure potential the time domain in which the delayed luminescence amount increases when the xylem pressure potential is decreased is the domain of (A). This time domain A differs according to the species of plant. The time domain A unique to the plant can be determined according to the species of plant by changing the xylem pressure potential. Also, a more optimal time domain A may be set in reference to results of prior measurement of a sample group that is clearly being stressed and a sample group that can be judged to be growing appropriately.

The data of the delayed luminescence amount acquired in step (a) suffice to be data acquired in the time domain A and, for example, may be data of the delayed luminescence amount at a predetermined point within the time domain A (for example, at 0.4 seconds after excitation light irradiation) or may be cumulative data of delayed luminescence amounts measured in a predetermined time interval within the time domain A (for example, an interval of 0.1 second to 2 seconds after excitation light irradiation). As the delayed luminescence amount data, it is preferable to use data acquired within a time domain of 0.01 to 5 seconds after excitation light irradiation. By using the delayed luminescence amount data within this time domain, vitality evaluation at higher accuracy is made possible. In particular, use of the delayed luminescence amount data within this time domain enables evaluation of acute stress at higher accuracy.

Figure 2:
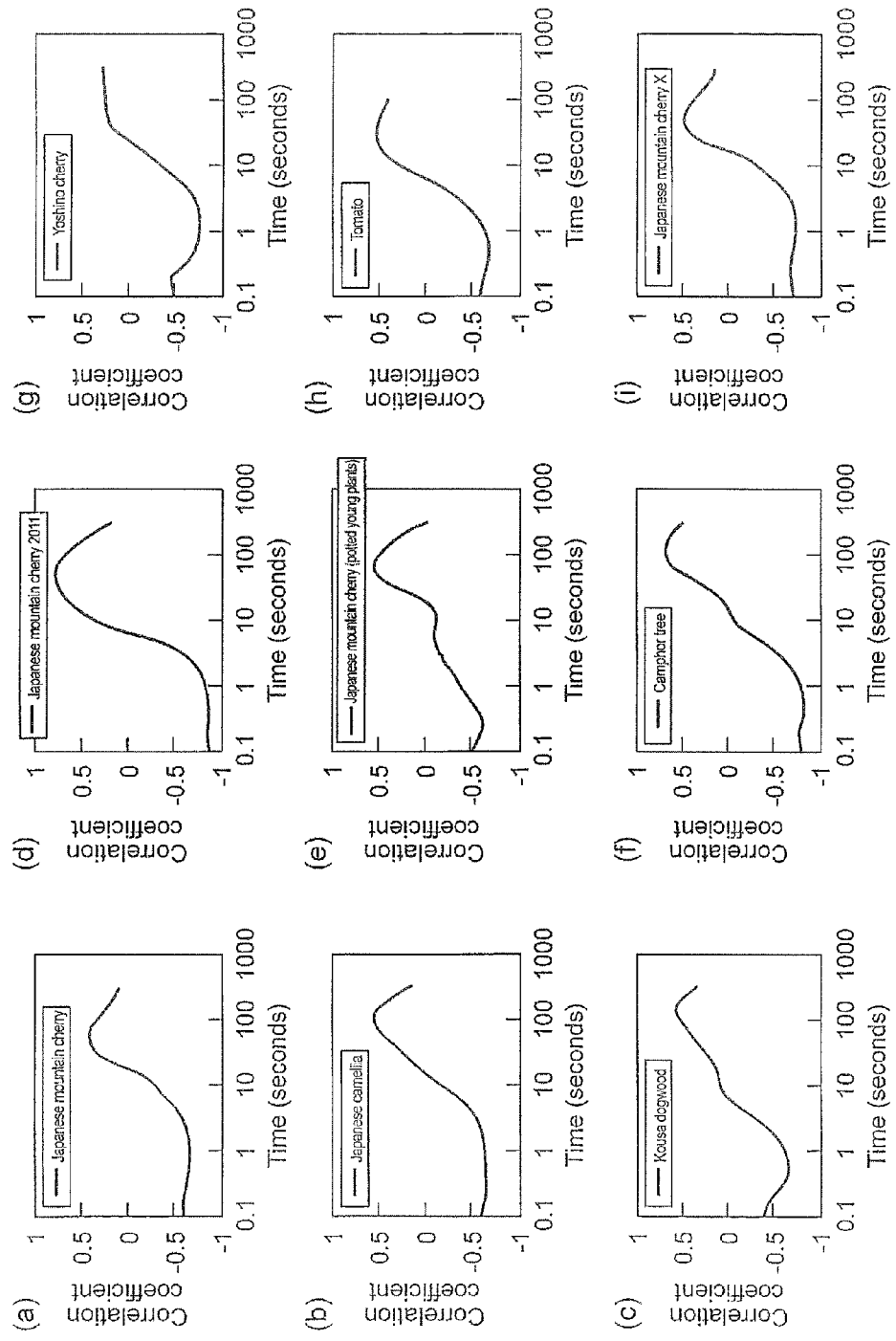
FIG. 2 shows graphs of a correlation coefficient of the delayed luminescence amount and water potential at respective measurement times in Example 1.

The data of the delayed luminescence amount acquired in step (a) are preferably data within a time domain in which an absolute value of a correlation coefficient of leaf water potential or other vitality index indicating the vitality state of the plant and the delayed luminescence amount is greater than an absolute value of a correlation coefficient of the vitality index and chlorophyll fluorescence (Fv/Fm) (may also be referred to hereinafter as "time domain B"). For example, as shown in FIG. 2, in one mode, the absolute value of the correlation coefficient of the leaf water potential and the delayed luminescence amount takes on a maximum value at an initial stage of measurement. In the vicinity of the maximum value, the absolute value of the correlation coefficient is greater than the absolute value of the correlation coefficient of the leaf water potential and the chlorophyll fluorescence (Fv/Fm) as shall be described below in regard to an example. The chlorophyll fluorescence (Fv/Fm) may be measured by a conventional method. For example, it may be measured by a pulse-modulated chlorophyll fluorescence measurement apparatus (for example, FluorPen100, made by Photon Systems Instruments). Fm is a maximum value of fluorescence intensity, Fo is a minimum value of fluorescence intensity, and Fv is Fm minus Fo. Fv/Fm represents a maximum yield of photosynthesis and is generally known to take a value of approximately 0.80 to 0.83 under optimal conditions in higher plants (see Kintake Sonoike, Methods for Photosynthesis Research (Chapter 4 Spectroscopic Measurement Part 3 Pulse-Modulated Fluorescence), Low Temperature Science, vol. 67, 2008, coedited by The Institute of Low Temperature Science, Hokkaido University and The Japanese Society of Photosynthesis Research, p. 507).

The time domain B differs according to the species of plant. The time domain B unique to the plant can be determined according to the species of plant by comparing the absolute value of the correlation coefficient of the leaf water potential and the delayed luminescence amount and the absolute value of the correlation coefficient of the leaf water potential and the chlorophyll fluorescence (Fv/Fm).

The time domain B may, for example, be the time domain of 0.01 second to 5 seconds after excitation light irradiation. The data of the delayed luminescence amount in the time domain B may, for example, be data of the delayed luminescence amount at a specific point within the time domain B (for example, at 0.4 seconds) or may be cumulative data of delayed luminescence amounts measured in a specific time interval within the time domain B (for example, an interval of 0.1 second to 5 second). The time domain B may, for example, be a time domain of 0.05 seconds to 4 seconds, a time domain of 0.1 second to 3 seconds, or a time domain of 0.1 second to 2 seconds after excitation light irradiation. Also, the time domain B is preferably a time domain of ±1 second, more preferably a time domain of ±0.5 seconds, and even more preferably a time domain of ±0.1 second centered at a time at which the maximum value is exhibited.

(Second Embodiment,(a') Step)

With the method for evaluating vitality according to the second embodiment of the present invention, in the (a') step of acquiring the data of the specific delayed luminescence amount, the delayed luminescence of a leaf is measured for each plant of a group of plants subject to evaluation to obtain the data of the delayed luminescence amount in the time domain of 10 to 50 seconds after excitation light irradiation.

As the group of plants subject to evaluation, the same plant group as that of the first embodiment may be subject to evaluation.

In the second embodiment, the data of the delayed luminescence amount acquired in step (a') suffice to be data in the time domain of 10 to 50 seconds after excitation light irradiation, and, for example, may be data of a delayed luminescence amount at a specific point within the range (for example, at 30 seconds after excitation light irradiation) or may be cumulative data of delayed luminescence amounts measured in a specific time interval within the range (for example, an interval of 25 seconds to 35 seconds after excitation light irradiation). It is especially preferable to use data of a delayed luminescence amount acquired within a time domain of 20 to 40 seconds after excitation light irradiation. Also, the time domain is preferably set to a time domain of ±10 seconds, more preferably a time domain of ±5 seconds, and even more preferably a time domain of ±1 second centered at a time at which a maximum value is exhibited.

Figure 5:
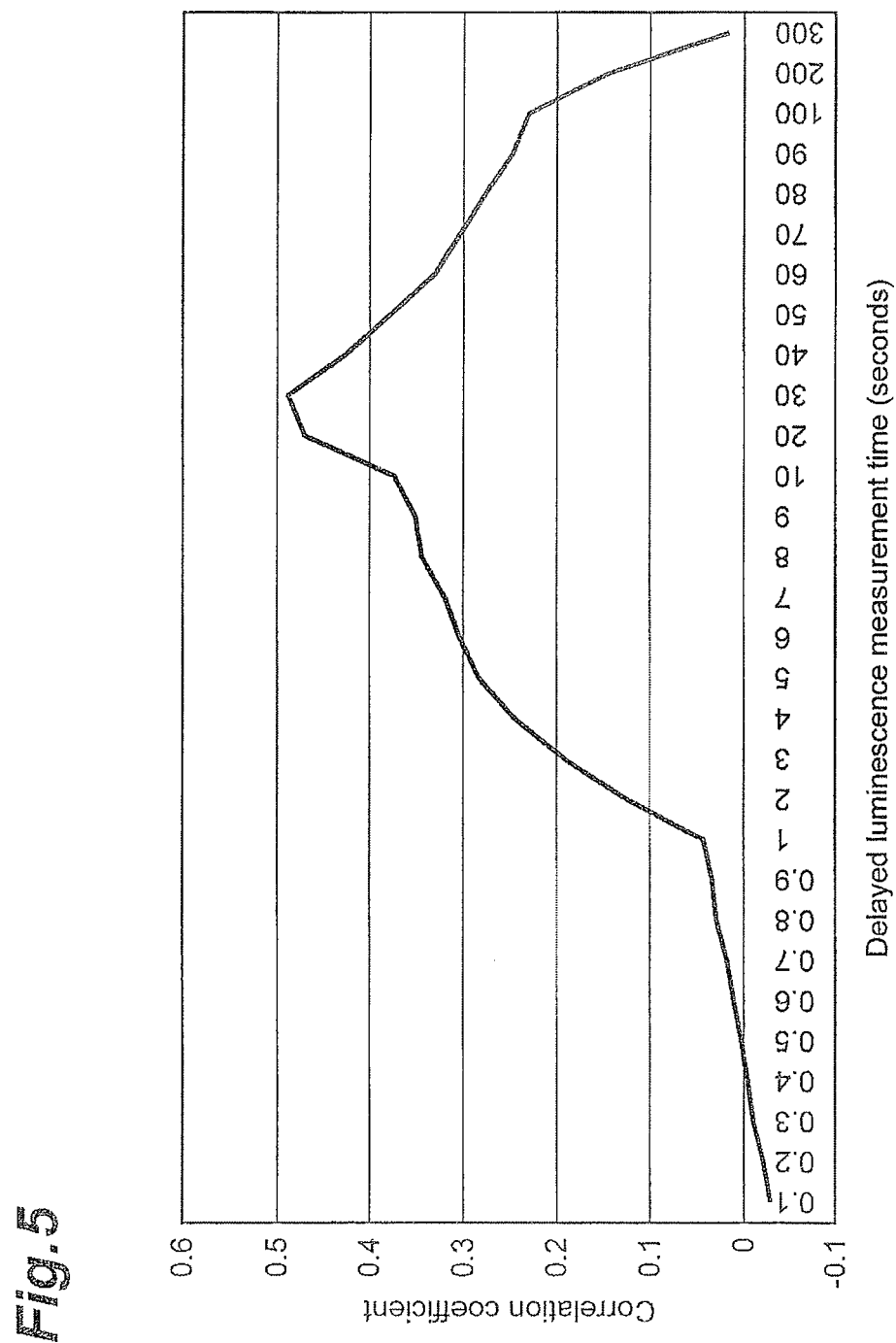
FIG. 5 is a graph of a correlation coefficient of the delayed luminescence amount and the terminal branch growth increment in Example 2.

The data of the delayed luminescence amount acquired in step (a') are preferably data within a time domain (time domain B) in which an absolute value of a correlation coefficient of terminal branch growth increment or other vitality index indicating the vitality state of the plant and the delayed luminescence amount is greater than an absolute value of a correlation coefficient of the vitality index and chlorophyll fluorescence (Fv/Fm). In the evaluation method according to the second embodiment, for example, as shown in FIG. 5, the absolute value of the correlation coefficient of the terminal branch growth increment, which is a vitality index that reflects chronic stress, and the delayed luminescence amount takes on a maximum value at a comparatively late stage of measurement. In the present example, the absolute value of the correlation coefficient increases rapidly from approximately 1 second after excitation light irradiation, exhibits a maximum value at around 30 seconds, thereafter exhibits a decreasing trend, and the correlation coefficient decreases again at approximately 300 seconds. The absolute value of the correlation coefficient in the vicinity of the maximum value is greater than the absolute value of the correlation coefficient of the terminal branch growth increment or other vitality index reflecting chronic stress and the chlorophyll fluorescence (Fv/Fm).

The time domain B differs according to the species of plant. The time domain B unique to the plant can be determined according to the species of plant by comparing the absolute value of the correlation coefficient of the vitality index reflecting chronic stress and the delayed luminescence amount, and the absolute value of the correlation coefficient of the vitality index reflecting chronic stress and the chlorophyll fluorescence (Fv/Fm).

The method for evaluating vitality according to the second embodiment is considered to be suited, for example, to evaluating the vitality of a plant based on correlation with respect to an index of long-term growth in the field. "Long-term" refers, for example, to months, seasons, or years. Examples of such a growth index include branch growth increment, trunk growth increment, vitality evaluation rank according to expert, etc. In the method for evaluating vitality according to the second embodiment, the long-term growth index may be a vitality index that reflects chronic stress. The vitality index reflecting chronic stress is preferably the terminal branch growth increment. The terminal branch growth increment can be obtained by measuring the length of growth of one or more of terminal branches in the current year.

In each of the methods for evaluating vitality according to the first and second embodiments, a leaf collected from the plant may be used or a leaf growing on the plant may be used directly in measuring the delayed luminescence.

Although the temperature condition of the delayed luminescence measurement is not restricted in particular as long as it is fixed during the measurement, it is preferably 5 to 35° C. and more preferably 20 to 30° C.

The delayed luminescence measurement may be performed by a known apparatus and method, for example, the apparatus and method described in WO2005/062027. As a more predetermined example, a method of performing a dark treatment followed by excitation light irradiation on a leaf of the plant and thereafter measuring the weak luminescence emitted by the leaf of the plant under a dark condition can be cited. As the apparatus for this purpose, for example, a weak luminescence measurement apparatus that includes an excitation light source and a photomultiplier tube or a high sensitivity camera system, etc., may be used.

The duration of performing the dark treatment on the leaf of the plant is preferably 5 to 1200 seconds and more preferably 150 to 600 seconds.

The wavelength of the excitation light irradiated onto the leaf of the plant is preferably 280 to 900 nm and more preferably 400 to 750 nm.

The duration of irradiation of the excitation light onto the leaf of the plant may be 0.1 to 60 seconds or may be 0.5 to 20 seconds. It may also be 20 to 300 seconds or may be 30 to 100 seconds.

In measuring the delayed luminescence, the area of the leaf exposed to a delayed luminescence detector is preferably a predetermined area. The predetermined area, although not restricted in particular, is preferably 0.15 to 80 $cm^2$ and more preferably 0.5 to 10 $cm^2$.

<First Embodiment,(b) Step>

With the method for evaluating vitality according to the first embodiment of the present invention, in the (b) step of processing the plurality of the data items obtained to evaluate a portion of individual plants as individuals of good growth or poor growth, the data of the plurality of delayed luminescence amounts obtained are processed to evaluate a plant exhibiting a delayed luminescence amount not less than the preset upper limit threshold as an individual of poor growth or evaluate a plant exhibiting a delayed luminescence amount not more than the preset lower limit threshold as an individual of good growth. This step may be one in which by evaluating individual plants as being of good growth or poor growth, the individual plants are selected as individual plants of poor growth or good growth.

As mentioned above, the delayed luminescence amount obtained in step (a) is negatively correlated with the leaf water potential. That is, when the delayed luminescence amount is high, the leaf water potential is low and oppositely when the delayed luminescence amount is low, the leaf water potential is high. Therefore, in the group of plants subject to selection, an individual (group) of high delayed luminescence amount tends to be poor in growth state and an individual (group) of low delayed luminescence amount tends to be good in growth state.

From such a standpoint, the method for processing (analyzing) the data of the delayed luminescence amounts is not restricted as long as it is a method by which an individual plant with the delayed luminescence amount being not less than the preset upper limit threshold or an individual plant with the delayed luminescence amount being not more than the preset lower limit threshold can be identified. The upper limit threshold and the lower limit threshold are set as suited in accordance with the data processing (analyzing) method, the purpose of selection, etc.

Examples of methods for processing (analyzing) the data of the delayed luminescence amounts to select or evaluate individual plants include but are not restricted to the following methods of (i) to (iii).

(i) Ranking

The data are ranked based on the delayed luminescence amount and individual plants within a range of the top X % (for example, the top 10% when ranking is performed in the order of decreasing delayed luminescence amount) or the bottom X % (for example, the bottom 10% when ranking is performed in the order of decreasing delayed luminescence amount) are identified and selected or evaluated. For example, if ranking is performed in the order of decreasing delayed luminescence amount, the top 10% can be identified and selected or evaluated as individual plants of poor growth. Or, the bottom 10% can be identified and selected or evaluated as individual plants of good growth. The upper limit threshold and the lower limit threshold in this case are the top 10% and the bottom 10%, respectively. With this method, a specific number of samples is always selected or evaluated, and therefore the method is effective in a case where a predetermined number of samples of good growth or poor growth are to be identified in a forest or farm, such as in cases of thinning or culling or in cases where saplings, mature trees, or crops of good growth are to be selected as commodities.

(ii) Use of a Normal Distribution

The data of a population are assumed to follow a normal distribution and a Y % prediction interval (the range for which the prediction of which range the sample values to be observed in the future will fall within is performed) is calculated. If the measured values so far do not fall within the Y % prediction interval, the individual plant is identified and selected or evaluated as being an individual of good or poor growth. For example, when Y=80, the ranges at the respective ends outside the prediction interval are respectively 10%, and if the measured values so far do not fall within the 80% prediction interval, the sample can be identified and selected or evaluated as being of good growth (top 10%) or poor growth (bottom 10%).

(iii) Use of a Bootstrap Method

By a bootstrap method (a method in which sampling with replacement is performed repeatedly on a single sample to generate a large quantity of samples and an estimate value is calculated from the samples thus generated to analyze a property of a population, an error of estimation by a model, etc.), respective confidence intervals (for example, 95% confidence intervals) of a $Z_1$ percentile value (for example, a 10 percentile value) and a $Z_2$ percentile value (for example, a 90 percentile value) of the population are estimated. If the measured values so far do not fall within an interval sandwiched by the confidence interval of the $Z_1$ percentile value and the confidence interval of the $Z_2$ percentile value, the sample is identified and selected or evaluated as being of good growth (top 10%) or poor growth (bottom 10%).

Figure 3:
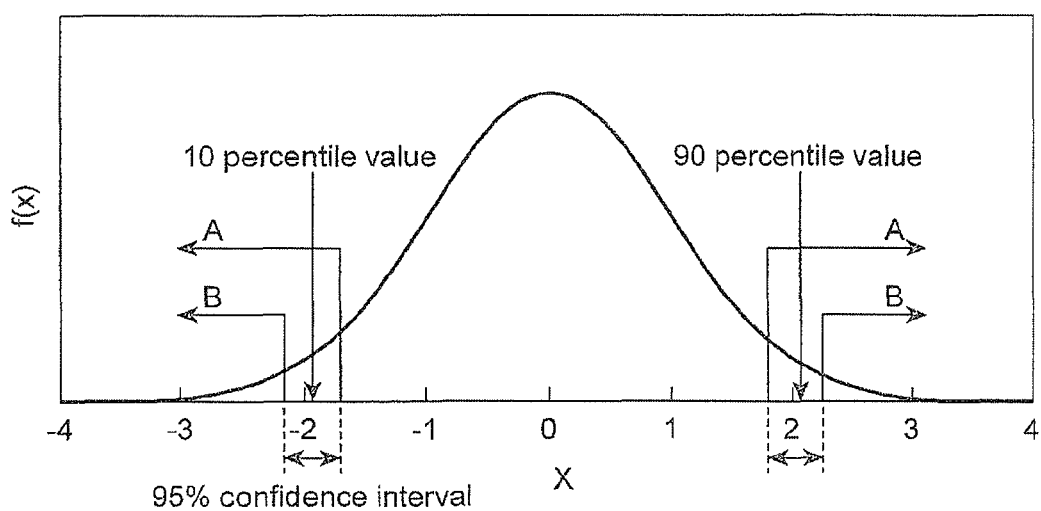
FIG. 3 is a diagram for describing a method for identifying a good growth sample or a poor growth sample (Method 3-1 and Method 3-2) in Example 1.

With the method of (iii), individual plants may be identified to be of good growth or poor growth with the inclusion of the individuals within the 95% confidence interval of the 10 percentile value (or the 90 percentile value) (range indicated by an arrow A in FIG. 3) or individual plants may be identified to be of good growth or poor growth without including the individuals within the 95% confidence interval of the 10 percentile value (or the 90 percentile value) (range indicated by an arrow B in FIG. 3).

With the methods of (ii) and (iii), the number of individual plants that are selected or evaluated as being of good or poor growth changes depending on the measured sample group because good or poor growth is identified while taking into consideration the variation of data. Then, the characteristics of the group can be examined from the variation of data. This is effective, for example, if the growth state of the plants in a certain region is to be characterized at the same time.

With the methods of (i), (ii), and (iii), any two may be used in combination or all three may be used in combination. By selecting or evaluating the individual plants that are identified as being of good or poor growth by all of the methods used in combination, it becomes possible to select or evaluate individuals that are more significantly good or poor in growth.

(Second Embodiment,(b')Step)

With the method for evaluating vitality according to the second embodiment of the present invention, in the (b') step of processing the plurality of the data items obtained to evaluate a portion of individual plants as individuals of good or poor growth, the data of the plurality of delayed luminescence amounts obtained are processed to evaluate a plant exhibiting a delayed luminescence amount not less than the preset upper limit threshold as an individual of good growth or evaluate a plant exhibiting a delayed luminescence amount not more than the preset lower limit threshold as an individual of poor growth. This step may be one in which by evaluating individual plants as being of good growth or poor growth, the individual plants are selected as individual plants of good growth or poor growth.

The delayed luminescence amount obtained in step (a') is positively correlated with the terminal branch growth increment. That is, when the delayed luminescence amount is high, the terminal branch growth increment is high and oppositely when the delayed luminescence amount is low, the terminal branch growth increment is low. Therefore, in the group of plants subject to selection, individuals (group) of high delayed luminescence amount tend to be good in growth state and individuals (group) of low delayed luminescence amount tend to be poor in growth state.

In the second embodiment, the method for processing (analyzing) the data of the delayed luminescence amounts is not restricted as long as it is a method by which an individual plant with the delayed luminescence amount being not less than the preset upper limit threshold or an individual plant with the delayed luminescence amount being not more than the preset lower limit threshold can be identified. The upper limit threshold and the lower limit threshold are set as suited in accordance with the data processing (analyzing) method, the purpose of selection, etc.

As examples of methods for processing (analyzing) the data of the delayed luminescence amounts to evaluate or select individual plants, the methods of (i) to (iii) in the first embodiment may be used. For example, with the method of (i), the same procedure as that in the case of the first embodiment may be performed, except that the data are ranked based on the delayed luminescence amount and identifying and evaluating or selecting the top X % as individual plants of good growth and identifying and evaluating or selecting the bottom X % as individual plants of poor growth.

The vitality of a plant decreases upon receiving the influence of stress. Drought, high temperature, freezing, oligotrophy, deficiency of microelements, salt damage, disease and insect damage, etc., can be cited as examples of stress. With the method for evaluating vitality according to the first embodiment, the vitality is preferably that which reflects the influence of acute stress, particularly drought stress. With the method for evaluating vitality according to the second embodiment, the vitality is preferably that which reflects the influence of chronic stress.

The method for evaluating vitality according to the first embodiment may further comprise (c) a step of measuring a chlorophyll amount of the plant leaf to obtain chlorophyll amount data and (d) a step of calculating data of corrected delayed luminescence amount by correcting the data of delayed luminescence amount obtained in step (a) by the chlorophyll amount per predetermined area. In a case where the step (c) and the step (d) are included, it is preferable to use the data of the corrected delayed luminescence amounts in place of the data of the delayed luminescence amounts in step (b).

In step (c), the chlorophyll amount in the plant leaf is measured to acquire the chlorophyll amount data.

The method for measuring the chlorophyll amount is not restricted in particular as long as it is a known method, and a method using reflected light obtained by irradiating light onto the plant leaf as described in JP2011-38879 or a method using transmitted light obtained by irradiating light onto the plant leaf as implemented in the SPAD-502 Chlorophyll Meter (made by Konica Minolta, Inc.) is preferably used.

In a case of measuring the chlorophyll amount using reflected light or transmitted light, the area of the leaf exposed to a detector of reflected light or transmitted light is preferably a predetermined area. Step (d) can thereby be performed more simply. The predetermined area is not restricted in particular and is preferably 0.06 to 80 cm$^2$ and more preferably 0.5 to 10 cm$^2$.

In step (d), the data of the delayed luminescence amount obtained in step (a) are corrected by the chlorophyll amount per predetermined area to calculate the data of the corrected delayed luminescence amount.

The data of the corrected delayed luminescence amount are obtained, for example, by division by the chlorophyll amount per predetermined area of the plant leaf. The data (S) of the corrected delayed luminescence amount may also be calculated by the following formula.

$$S = \left(\frac{T \times e - f}{U \times g - h}\right)$$ [Numerical Formula 1]

T: Delayed luminescence amount
U: Chlorophyll amount per predetermined area
e, g: Weighting of the delayed luminescence amount and chlorophyll amount values
f, h: Baselines of the measured value of the delayed luminescence and the measured value of the chlorophyll amount (Third and Fourth Embodiments)

A method for evaluating vitality of a plant according to a third embodiment of the present invention comprises a step of measuring delayed luminescence amounts of a leaf of a plant subject to evaluation at x seconds and y seconds after excitation light irradiation (where, x and y are positive real numbers and x≠y) to obtain two data items $D_{x1}$ and $D_{x2}$ delayed luminescence amount, a step of obtaining a operated value by any of the following formulae (1), (2), and (3) using $D_{x1}$ and $D_{x2}$, and a step of evaluating a vitality state of the plant by comparing the calculated value thus obtained and a predetermined threshold.

$O = D_{x1}/D_{x2}$ (1)

$O = D_{x1} - D_{x2}$ (2)

$O = (D_{x1} - D_{x2})/(D_{x1} + D_{x2})$ (3)

[In the formulae (1), (2), and (3), $D_{x1}$ represents the delayed luminescence amount data item at x seconds after excitation light irradiation, $D_{x2}$ represents the delayed luminescence amount data item at y seconds after excitation light irradiation, and O represents the calculated value.]

With the method for evaluating vitality of a plant according to the third embodiment, evaluation of vitality at even higher accuracy is made possible regardless of whether the "predetermined threshold" is a threshold set based on a vitality index that reflects acute stress or is a threshold set based on a vitality index that reflects chronic stress. That is, the method for evaluating vitality of a plant according to the third embodiment may be a method for evaluating acute stress of a plant or a method for evaluating chronic stress of a plant.

A method for evaluating vitality of a plant according to a fourth embodiment of the present invention comprises a step of measuring a delayed luminescence amount of a leaf of a plant subject to evaluation at a plurality of points in a preset time domain to obtain a plurality of data items of delayed luminescence amount, a step of approximating a relationship between elapsed time X after excitation light irradiation and the corresponding delayed luminescence amount Y by a curve approximation formula using the plurality of delayed luminescence amount data items to obtain at least one value, selected from the group consisting of constants in the approximation formula, as a coefficient value, and a step of evaluating a vitality state of the plant by comparing the coefficient value thus obtained and a predetermined threshold.

With the method for evaluating vitality of a plant according to the fourth embodiment, evaluation of vitality at even higher accuracy is made possible regardless of whether the "predetermined threshold" is a threshold set based on a vitality index that reflects acute stress or is a threshold set based on a vitality index that reflects chronic stress. That is, the method for evaluating vitality of a plant according to the fourth embodiment may be a method for evaluating acute stress of a plant or a method for evaluating chronic stress of a plant.

(Third Embodiment, Step of Obtaining Data of Delayed Luminescence Amounts and Step of Obtaining Index Value)

With the method for evaluating vitality according to the third embodiment of the present invention, in the step of obtaining the data of the specific delayed luminescence amounts, the delayed luminescence amount of a leaf of a plant subject to evaluation is measured at x seconds and y seconds after excitation light irradiation (may also be referred to hereinafter as the "first time" and the "second time," respectively; x and y may be of the reverse order) to obtain the two delayed luminescence amount data items $D_{x1}$ and $D_{x2}$. x and y are positive real numbers and x≠y. $D_{x1}$ and $D_{x2}$ are delayed luminescence amount data items of the same individual plant.

Each of the time domains in which the delayed luminescence amounts are measured may be any time domain as long as it is one in which delayed luminescence can be measured after excitation light irradiation. For example, the first time may be set in a time domain in which the delayed luminescence amount increases when the xylem pressure potential is decreased (time domain A) and the second time may be set after the elapse of the time domain A, or both the first and second times may be set within the time domain A, or both the first and second times may be set after the elapse of the time domain A. The time domain A thus does not have to be specified to select the times at which the delayed luminescence is measured. If the time domain A is specified and vitality evaluation is to be performed based on a vitality index that reflects acute stress, it is preferable to set the first time within the time domain A and the second time after the elapse of the time domain A or to set both the first and second times within the time domain A and it is more preferable to set both the first and second times within the time domain A. By setting the measurement times in these time domains, the accuracy of evaluation can be improved further.

In regard to the times at which the delayed luminescence amounts are to be measured, if vitality evaluation is to be performed based on a vitality index that reflects acute stress, the x and y may be set in a time domain in 0.2 to 1.00 seconds after excitation light irradiation, and may be set, for example, in a time domain in 0.8 to 20 seconds. The x and y are preferably set in a time domain in 0.8 to 5 seconds after excitation light irradiation. If vitality evaluation is to be performed based on a vitality index that reflects chronic stress, the x and y are preferably set in a time domain in 10 to 300 seconds after excitation light irradiation. By setting the measurement times in these time domains, the accuracy of evaluation can be improved further.

Besides adjusting the times of measurement as described above, the specific method for measuring the delayed luminescence amounts in the method for evaluating vitality according to the third embodiment may be the same as the measurement method in the method for evaluating vitality according to the first or second embodiment.

In the method for evaluating vitality according to the third embodiment, the two delayed luminescence amount data items $D_{x1}$ and $D_{x2}$ obtained are used to perform a division, subtraction, or normalized difference type operation to obtain an operated value as an index value. The calculation formulae representing the respective operation method are the following formulae (1), (2), and (3).

$$O=D_{x1}/D_{x2} \tag{1}$$

$$O=D_{x1}-D_{x2} \tag{2}$$

$$O=(D_{x1}-D_{x2})/(D_{x1}+D_{x2}) \tag{3}$$

[In the formulae (1), (2), and (3), $D_{x1}$ represents the delayed luminescence amount data item at x seconds after excitation light irradiation, $D_{x2}$ represents the delayed luminescence amount data item at y seconds after excitation light irradiation, and O represents the calculated value.]

The plant to be subject to evaluation may be a single individual plant or may be a plurality of plants in a plant group.

Each of the operated values obtained by the respective formulae above indicates a relationship between delayed luminescence amount data items measured at two different times for the same individual plant and indicates a attenuation rate or attenuation amount of the delayed luminescence amount of the plant in a specific time domain. In a process of thus obtaining the operated value from the original data of the delayed luminescence amounts, problems, such as scattering of measured values due to noise, difference in measurement sensitivity among apparatuses used, absolute errors of output values, etc., can be alleviated. A relative evaluation of a plurality of plants thus does not have to be performed necessarily, evaluation of a plant is possible with a single individual, and the labor of collecting data of multiple samples is not required necessarily.

(Fourth Embodiment, Step of Obtaining Data of Delayed Luminescence Amounts and Step of Obtaining Index Value)

With the method for evaluating vitality according to the fourth embodiment of the present invention, in the step of obtaining the data of the specific delayed luminescence amounts, the delayed luminescence amounts of a leaf of a plant subject to evaluation at a plurality of points in a preset time domain are measured.

The time domain in which the delayed luminescence amounts are measured may be any time domain as long as it is one in Which delayed luminescence can be measured after excitation light irradiation. For example, the time domain may be a portion of a time domain inside a time domain in which the delayed luminescence amount increases when the xylem pressure potential is decreased (time domain A) or may be a portion of a time domain after the elapse of the time domain A, or may be a time domain spanning from the time domain A to after the elapse of the time domain A. The time domain A thus does not have to be specified to select the time domain in which the delayed luminescence is measured. If the time domain A is specified and vitality evaluation is to be performed based on a vitality index that reflects acute stress, it is preferable to use a portion of a time domain inside the time domain A or a time domain spanning from the time domain A to after the elapse of the time domain A, and it is more preferable to use a portion of a time domain of inside the time domain A. By setting the times of measurement in these time domains, the accuracy of evaluation can be improved further.

If vitality evaluation is to be performed based on a vitality index that reflects acute stress, the time domain in which the delayed luminescence amounts are to be measured may be set to a time domain included in a range of 0.1 to 100 seconds after excitation light irradiation, and may be set, for example, to a time domain included in a range of 0.8 to 20 seconds. The time domain in which the delayed luminescence amounts are to be measured is preferably set to a time domain included in a range of 0.7 to 5 seconds after excitation light irradiation. If vitality evaluation is to be performed based on a vitality index that reflects chronic stress, the time domain in which the delayed luminescence amounts are to be measured is preferably set to a time domain of 10 to 300 seconds after excitation light irradiation. By setting the time domain of measurement within the above ranges, the accuracy of evaluation can be improved further.

Besides adjusting the time domain of measurement as described above, the predetermined method for measuring the delayed luminescence amounts in the method for evaluating vitality according to the fourth embodiment may be the same as the measurement method in the method for evaluating vitality according to the first or second embodiment.

The step of obtaining the index value in the method for evaluating vitality according to the fourth embodiment may be a step of approximating a relationship between elapsed time X after excitation light irradiation and the corresponding delayed luminescence amount Y by a curve approximation formula using the obtained plurality of delayed luminescence amount data items to obtain at least one value, selected from the group consisting of constants in the approximation formula, as a coefficient value.

As the coefficient value, one or more values selected from the group consisting of constants a, b, c, d, e, and λ in the following formulae (4), (5), and (6) may be used.

$$Y=a \cdot b^X \tag{4}$$

$$Y=a \cdot e^{(-\lambda \cdot X)} \tag{5}$$

$$Y=c+d \cdot X+e \cdot X^2 \tag{6}$$

[In the formulae (4), (5), and (6), X and Y are the elapsed time X after excitation light irradiation in the preset time domain and the corresponding delayed luminescence amount Y.]

As an example of a method for approximating the data to any of the above approximation formulae and obtaining the coefficient value, the glm function of the statistical software R may be used.

The plant to be subject to evaluation may be a single individual plant or may be a plurality of plants in a plant group.

The coefficient value obtained by any of the approximation formulae above indicates a characteristic of attenuation of the delayed luminescence amount within a specific time. In a process of thus obtaining the coefficient value from the original data of the delayed luminescence amounts, problems, such as scattering of measured values due to noise, difference in measurement sensitivity among apparatuses used, absolute errors of output values, etc., can be alleviated.

A relative evaluation of a plurality of plants thus does not have to be performed necessarily, evaluation of a plant is possible with a single individual, and the labor of collecting data of multiple samples is not required necessarily.

With each of the methods for evaluating vitality according to the third and fourth embodiments, the operated value or coefficient value that is obtained as an index value is compared with the predetermined threshold to evaluate the vitality of the plant.

As the predetermined threshold, for example, an upper limit threshold, a lower limit threshold, or a combination of these may be set. Besides using, in place of the delayed luminescence amount itself, the operated value or the coefficient value obtained by using the delayed luminescence amount data, the method for evaluating by comparison with the threshold can be performed in the same manner as the evaluation method according to the first or second embodiment. That is, for example, an individual plant having a operated value or coefficient value not less than the preset upper limit threshold may be identified and evaluated or selected as an individual of good growth or poor growth, and an individual plant having a operated value or coefficient value not more than the preset lower limit threshold may be identified and evaluated or selected as an individual of good growth or poor growth. Whether to identify an individual to be of good growth or to identify an individual to be of poor growth differs according to whether the vitality index, such as the xylem pressure potential, terminal branch growth increment, etc., correlates positively or correlates negatively with the operated value or coefficient value (index value). In the case of positive correlation, a higher index value indicates better growth, and in the case of negative correlation, a higher index value indicates poorer growth.

Methods for identifying and evaluating or selecting individual plants based on the index value include but are not restricted to the above-described methods of (i) to (iii) as in the evaluation method according to the first or second embodiment.

As a method for setting the threshold, the threshold for a certain plant group may be set, for example, by measuring the vitality index of the plant, such as the xylem pressure potential, the terminal branch growth increment, etc., in advance together with the delayed luminescence amount data, calculating the respective index values using the delayed luminescence amount data, examining the correlation of the index values with the vitality index, and calculating an index value of a level corresponding to having or not having a desired vitality.

The vitality of a plant decreases upon receiving the influence of stress. Drought, high temperature, freezing, oligotrophy, deficiency of microelements, salt damage, disease and insect damage, etc., can be cited as examples of stress. With the method for evaluating vitality according to the third or fourth embodiment, the vitality may be that which reflects the influence of acute stress or that which reflects the influence of chronic stress.

If a vitality index that reflects the influence of acute stress is to be used, the method for evaluating vitality according to the third or fourth embodiment may further comprise a step of measuring a chlorophyll amount in the plant leaf to obtain chlorophyll amount data and a step of calculating data of corrected delayed luminescence amounts by correcting the obtained data of delayed luminescence amounts by the chlorophyll amount per predetermined area. In a case of calculating the data of corrected delayed luminescence amounts, it is preferable to use the data of the corrected delayed luminescence amounts in place of the data of the delayed luminescence amounts in the step of obtaining the operated value or the coefficient value.

In the method for evaluating vitality according to the present invention, by which of the methods of the respective embodiments described above the evaluation of vitality is to be performed may be set as appropriate in accordance with the species of plant subject to evaluation, the type of vitality index, etc. For example, a plurality of or all of the methods of the respective embodiments described above may be carried out in advance on a subject plant to select a method of high correlation with the vitality index. As predetermined examples, in cases where the xylem pressure potential (water potential) is used as the vitality index, the method according to the third embodiment (especially, the method using the subtraction type calculated value (formula (2)) as the index value) is the highest in correlation for camphor tree, Japanese camellia, Kousa dogwood, Japanese mountain cherry, and tomato, and the method according to the first embodiment (method using the data of the delayed luminescence amount in the time domain in which the delayed luminescence amount increases when the xylem pressure potential is decreased as the index) is the highest in correlation for Yoshino cherry.

[Measurement system] A measurement system for evaluating vitality of a plant according to the present embodiment (may also be referred to hereinafter simply as "measurement system") comprises at least a dark treatment tool and a measurement apparatus. Preferably, there are pluralities of the dark treatment tools.

The dark treatment tool has an opening capable of being opened and closed and shades a portion or all of a leaf of a plant. The dark treatment tool is preferably arranged so that the dark treatment can be performed on a portion or all of an individual leaf of a plant without cutting the individual leaf of the plant. The opening capable of being opened and closed may, for example, be a shutter mechanism.

Figure 13:
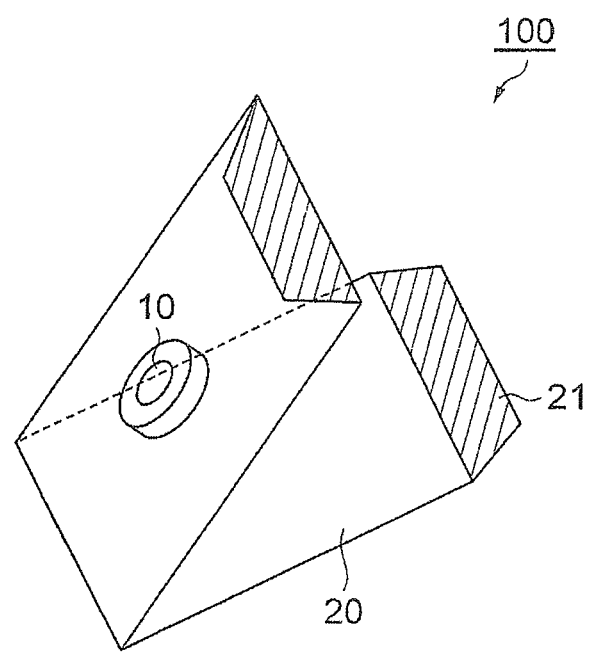
FIG. 13 is a schematic view of a dark treatment tool according to an embodiment.
Figure 14:
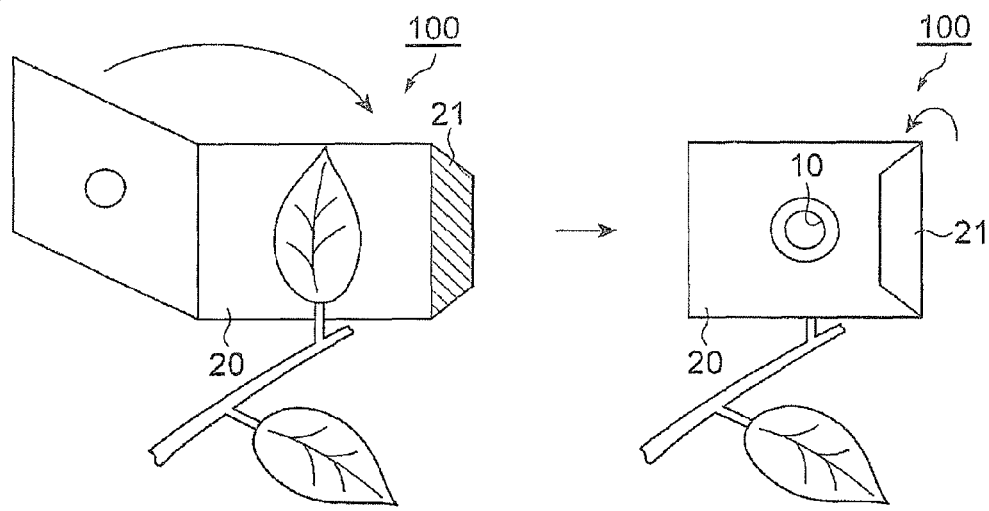
FIG. 14 shows explanatory diagrams of methods for using the dark treatment tool according to the embodiment.
Figure 14:
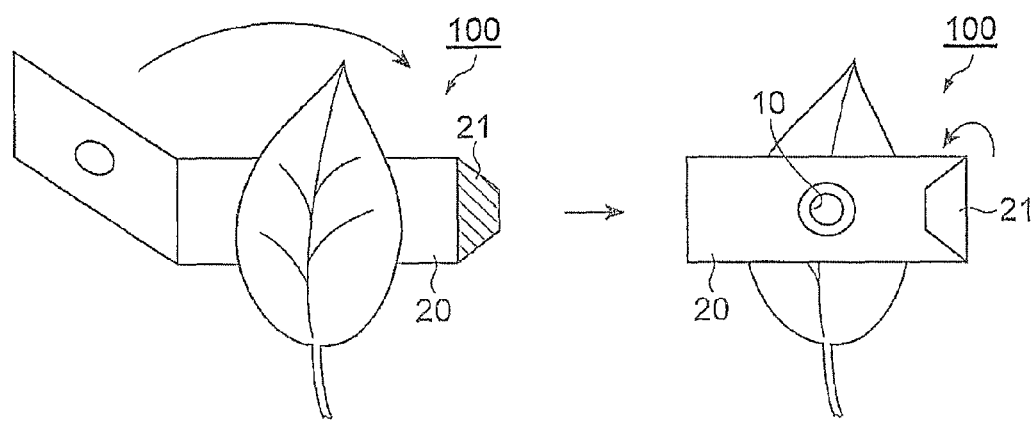
Figure 15:
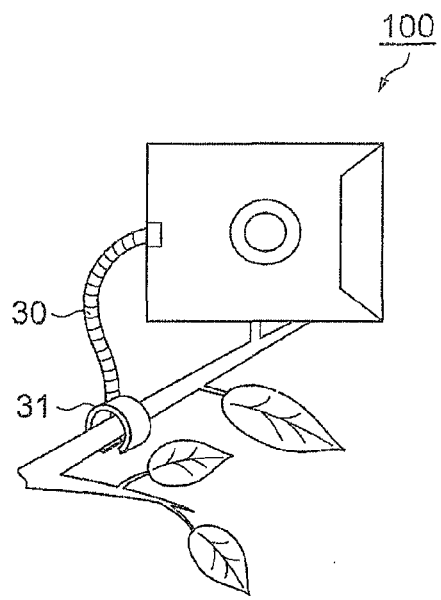
FIG. 15 shows explanatory diagrams of methods for using the dark treatment tool according to the embodiment.
Figure 15:
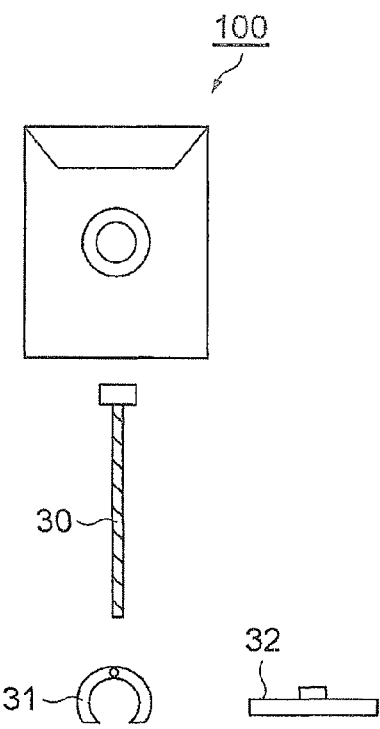
Figure 15:
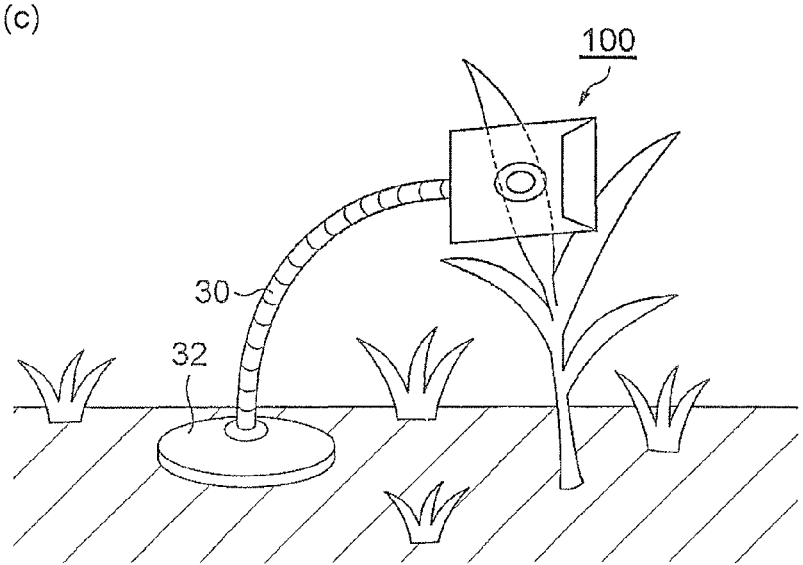

FIG. 13 is a schematic view of a dark treatment tool according to the embodiment. FIGS. 14 and 15 show explanatory diagrams of methods for using the dark treatment tool shown in FIG. 13.

The dark treatment tool 100 shown in FIG. 13 has a main body portion 20 and a shutter opening 10 arranged from a lightweight shutter mechanism. The dark treatment tool 100 covers and shades a portion or all of an individual leaf by means of the main body portion 20. The main body portion 20 is formed of a material of high shading property. Resin plates, thin metal plates of light weight, plates made of paper or wood, and aluminum foil can be cited as examples of the material forming the main body portion 20. It is further preferable for these materials to be coated in black so as not to allow passage of external light. Further, a material, having a shading property and yet being flexible to enable close contact with the plant surface to be achieved while avoiding damaging of the plant, is preferably used for the entirety of the inner surfaces of the main body portion 20 that sandwich a leaf or a periphery of the shutter opening 10 corresponding to a measured portion of the leaf. This can be realized, for example, by using foamed urethane or a rubber material and further disposing packings of similar material so as to surround the measured portion or arranging multiple packings in the form of pleats or further forming a maze-like structure with the same material to increase the shading property.

As shown in FIG. 14, the dark treatment tool 100 is used by folding the main body portion 20 so as to cover all (FIG. 14A) or a portion (FIG. 14B) of an individual leaf. After folding the main body portion 20, an end portion 21 of the main body portion 20 may be folded back and fixed. In this process, the shutter opening 10 is arranged to be positioned at the measured portion of the individual leaf. The measurement system may further include a shading means (not shown) that covers and thereby shades the individual leaf subject to measurement and leaves, branches, etc., in the surroundings. By including the shading means, the intensity of light in the surroundings of the individual leaf subject to measurement can be lowered to that of an indoor level when making a measurement outdoors under strong external light. The shading means may, for example, be a blackout curtain or a bag with a shading property; such as a bag of black color, etc.

As shown in FIG. 15, to hold the dark treatment tool 100 at an individual leaf of a tree, jigs 30 and 31 (FIGS. 15A and 15B) to be fastened to a branch or trunk or jigs 30 and 32 (FIGS. 15B and 15C) fixed to the ground may further be included.

After performing the dark treatment by shading the individual leaf with the dark treatment tool 100 (for example, for 300 seconds), a light collecting unit of the measurement apparatus and the shutter opening 10 are connected to perform measurement of delayed luminescence. Preferably, a plurality of the dark treatment tools 100 are prepared apart from the measurement apparatus. Dark treatment of an individual leaf to be subject to measurement subsequently can thereby be performed while measuring the delayed luminescence with the measurement apparatus and significant reduction of measurement time is made possible because measurement of the subsequent individual leaf can be started immediately after the end of measurement of a certain individual leaf.

The measurement apparatus has the light collecting unit capable of being attached to and detached from the opening of the dark treatment tool, a light source unit arranged to irradiate light onto the plant leaf, and a delayed luminescence detecting unit detecting the delayed luminescence of the plant leaf resulting from the light irradiated by the light source unit. The light collecting unit and the delayed luminescence detecting unit may be integral or may be separated as shall be described below.

Figure 16:
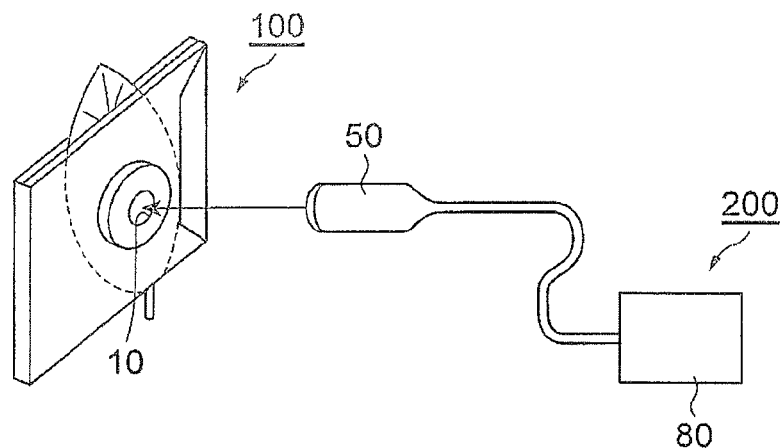
FIG. 16 shows explanatory diagrams of a method for using a measurement system according to the embodiment.
Figure 16:
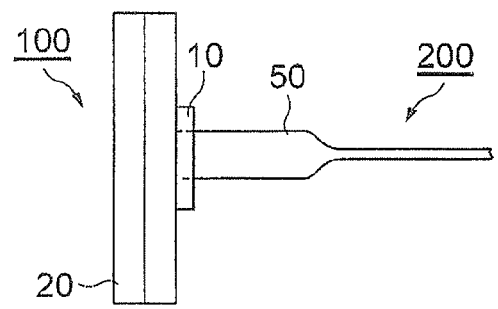
Figure 16:
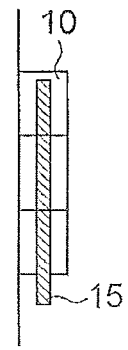
Figure 16:
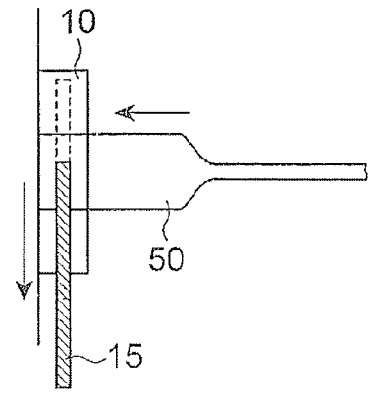
Figure 17:
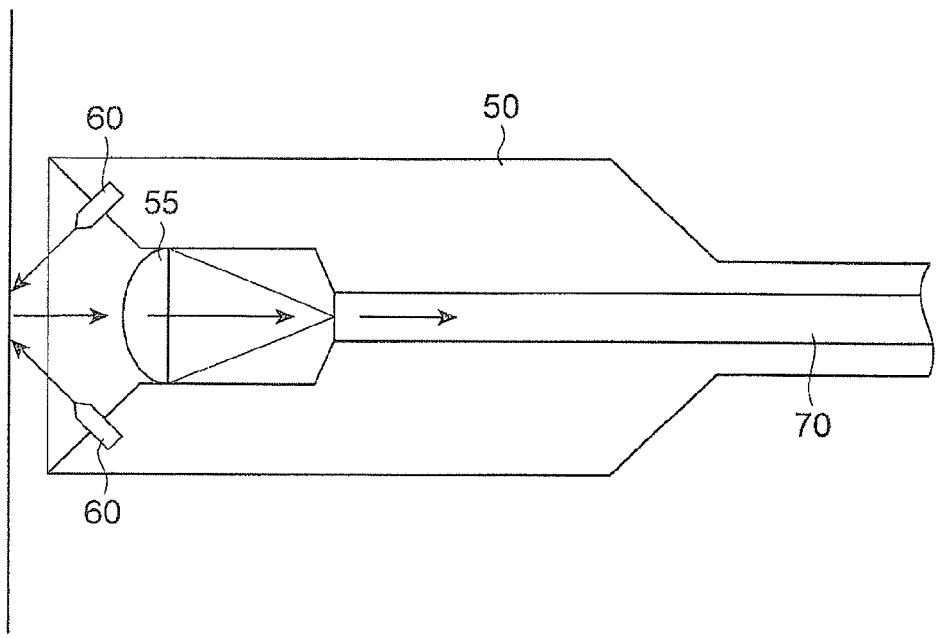
FIG. 17 is a schematic view of a measurement apparatus according to the embodiment.
Figure 18:
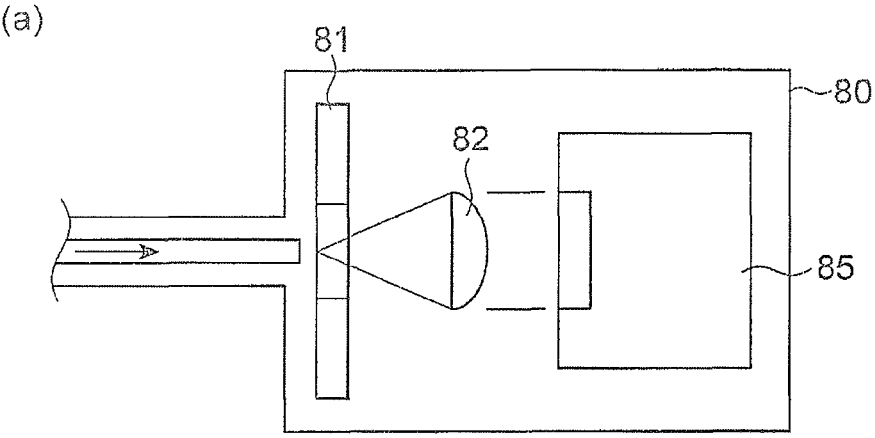
FIG. 18 shows schematic views of a plurality of embodiments of measurement apparatuses.
Figure 18:
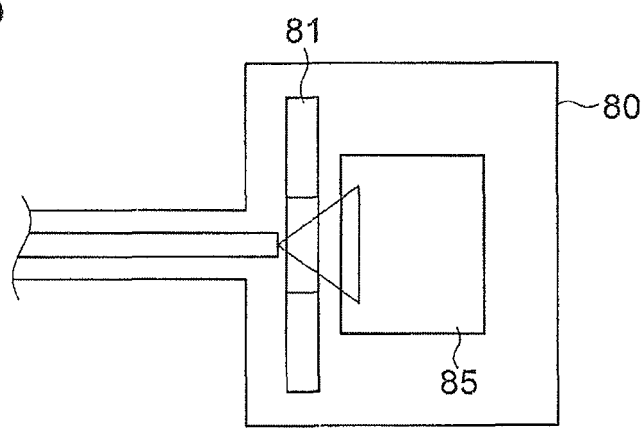
Figure 18:
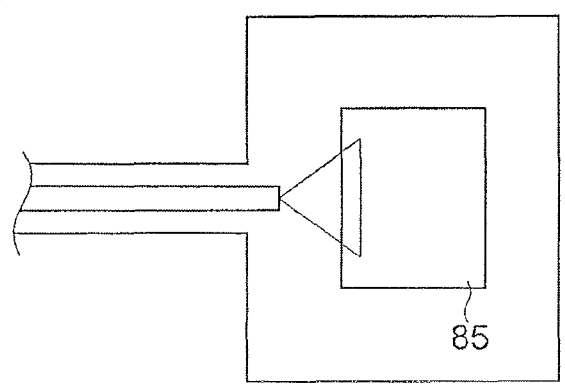
Figure 19:
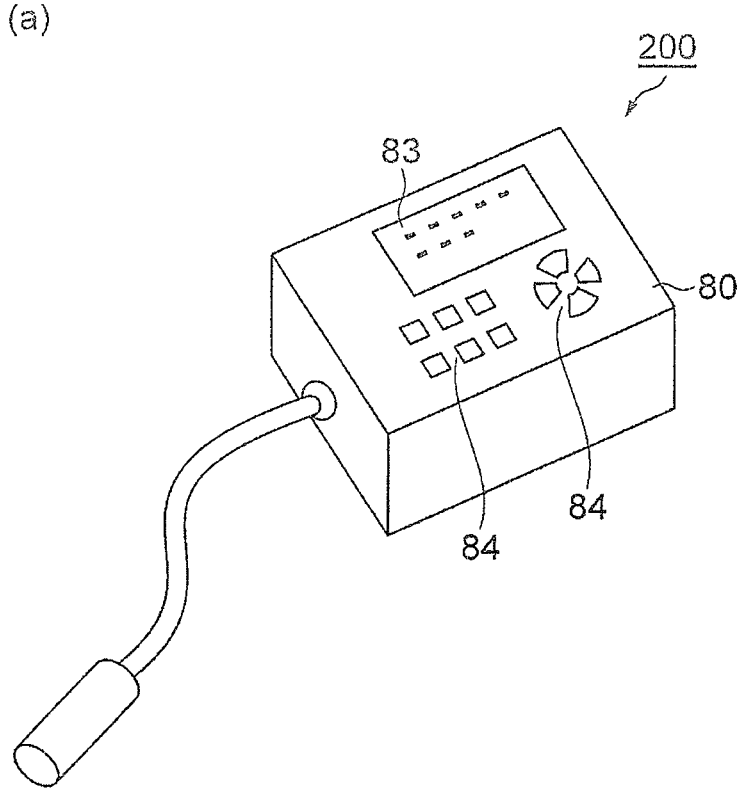
FIG. 19 shows schematic views of the measurement apparatus according to the embodiment.
Figure 19:
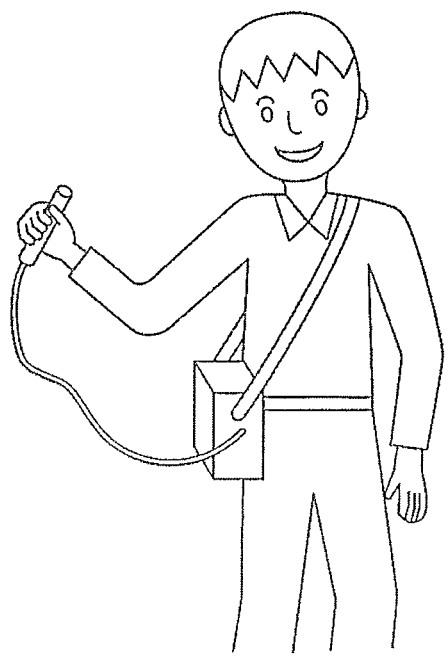

FIG. 16 shows explanatory diagrams of a method for using the measurement system according to the embodiment. FIG. 17 is a schematic view of a measurement apparatus according to the embodiment. FIG. 18 shows schematic views of a plurality of embodiments of measurement apparatuses. FIG. 19 shows schematic views of the measurement apparatus according to the embodiment.

The measurement system shown in FIG. 16A comprises the dark treatment tool 100 and the measurement apparatus 200. The measurement apparatus 200 has a light collecting unit 50, a light source unit 60 disposed in the light collecting unit 50, and a delayed luminescence detecting unit 80. It may also have a recording unit recording the data measured by the delayed luminescence detecting unit 80, an operating unit processing the measured data, an input unit inputting a processing method, and a control unit controlling actions of the light source unit 60, the delayed luminescence detecting unit 80, etc. As the recording unit, the operating unit, the input unit, and the control unit, a computer having the functions of these units may be used. The computer may be incorporated inside the measurement apparatus 20 or may be connected from the exterior.

The light collecting unit 50 is arranged to be connected to the shutter opening 10 of the dark treatment tool 100 and, after connection, the arrangement can be regarded as being an integral measurement apparatus without leakage of light that influences measurement (see FIG. 16B). A state enabling measurement is entered by connecting the light collecting unit 50 and the shutter opening 10 and opening the shutter. In this process, the shutter may be opened manually by a measurer or a mechanism that opens the shutter automatically upon connection may be included (see FIG. 16C and FIG. 16D). In the state where the shutter is opened, only a predetermined shape and area of the leaf are exposed.

The light collecting unit 50 includes an excitation light source (light source unit 60) for making the delayed luminescence be emitted. The light source unit 60 is arranged from a single or plurality of light sources capable of irradiating a plurality of wavelengths. That is, it is a multiple wavelength light source, such as a halogen lamp, or an arrangement combining a wavelength selection filter with such a light source, or an assembly of LEDs of different peak wavelengths, etc.

The light source unit 60 irradiates light of a specific wavelength onto the individual leaf. The wavelength is 400 nm to 1000 nm. Here, the light source unit 60 may be a monochromatic light source or a light source combining a plurality of light sources. The light emission by the light source unit 60 may be continuous for a predetermined duration or pulse lighting may be performed in any pattern. A plurality of light sources having the same or different wavelength characteristics may be made to emit light successively or the plurality of light sources may be made to emit light simultaneously. Also, a shutter that opens and closes in synchronization with the turning on and turning off of the light source may be combined to cut the afterglow of the light source.

As shown in FIG. 17 and FIG. 18, the leaf is excited by the light irradiated from the light source unit 60 and the delayed luminescence emitted from the leaf is guided to a photodetector 85 disposed in the delayed luminescence detecting unit 80. To transmit the delayed luminescence to the photodetector 85 efficiently in this process, a light collecting lens 55 may be included or an optical fiber or relay optical system 70 capable of relaying the delayed luminescence over a long distance may be used. By adopting the optical fiber or relay optical system 70 capable of relaying the delayed luminescence over a long distance, the light collecting unit 50 and the delayed luminescence detecting unit 80 are made separable to enable the light collecting unit 50 to be made compact and lightweight and thereby enable the work of measuring upon coupling to the dark treatment tool 100 attached to the individual leaf to be performed more efficiently.

As the photodetector 85 disposed in the delayed luminescence detecting unit 80, a photomultiplier tube, an avalanche photodiode, a silicon photodiode, etc., may be used. A shutter 81 for preventing the entry of excitation light may be disposed in front of the photodetector 85 (see FIGS. 18A and 18B). Also, the shutter may be omitted by performing control so that the photodetector 85 does not receive light during excitation light irradiation (see FIG. 18C).

A condenser lens 82 may further be disposed in front of the photodetector 85 to improve the light collecting efficiency (see FIG. 18A). Positioning of the condenser lens 82 is effective in the case where the optical fiber or relay optical system 70 is used.

As shown in FIG. 19, the delayed luminescence detecting unit 80 may have a display unit 83, arranged to display information during measurement, and an input unit 84 with a button, etc., arranged to operate the measurement apparatus (see FIG. 19A). If the measurement apparatus is compact and lightweight so as to be portable, a measurer can be outfit with the apparatus and can make measurements while moving. For this purpose, a belt or strap for outfitting may be mounted on the light collecting unit or the detecting unit (see FIG. 19B).

The measurement apparatus may have a mechanism that outputs a message indicating that data are insufficient until data of enough amounts enabling selection are collected with high reliability and accuracy.

In addition to the above arrangement, the measurement apparatus may further have a photodetecting unit detecting light that arises as a result of the light irradiated by the light source unit and reflects the chlorophyll amount in the plant leaf, and a recording unit recording the data of the delayed luminescence amount corresponding to the delayed luminescence detected by the delayed luminescence detecting unit and recording chlorophyll amount data corresponding to the light reflecting the chlorophyll amount and detected by the photodetecting unit. The photodetecting unit and the recording unit may be apparatuses that are independent of the measurement apparatus.

By the above-described dark treatment tools, which enable the dark treatment to be performed on a plurality of leaves in advance, and the compact, lightweight measurement apparatus that is portable, delayed luminescence measurement can be performed in a short time without cutting the individual leaf of the plant and a problem of error arising due to the cutting of the leaf can be resolved.

(Vitality Evaluation System)

Figure 20:
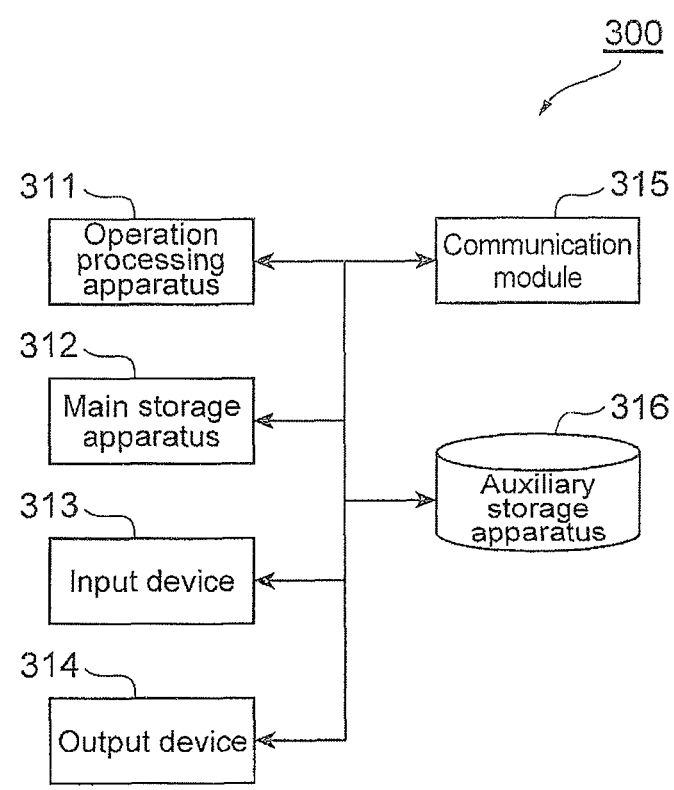
FIG. 20 is an outline diagram of the hardware arrangement of a vitality evaluation system.

The arrangement of a vitality evaluation system 300 shall now be described. FIG. 20 is an outline diagram of the hardware arrangement of the vitality evaluation system 300, and FIG. 21 is an outline diagram of the functional arrangement of the vitality evaluation system 300.

As shown in FIG. 20, the vitality evaluation system 300 is physically arranged as an ordinary computer that includes an operation processing unit 311, such as a CPU, etc., a main storage apparatus 312, such as a ROM, RAM, etc., an input device 313, such as a keyboard and mouse, etc., an output device 314, such as a display, etc., a communication module 315, such as a network card, etc., arranged to perform transmission and reception of data with a portable device, such as a smartphone equipped with a wireless function, etc., or a computer in USB connection, an auxiliary storage apparatus 316, such as a hard disk, etc. The respective functions of a vitality evaluation apparatus to be described in detail later are realized by making predetermined computer software be read onto the hardware of the operation processing unit 311, the main storage apparatus 312, etc., to make the input device 313, the output device 314, and the communication module 315 operate and reading and writing of data in the main storage apparatus 312 and the auxiliary storage apparatus 316 be performed under the control of the operation processing unit 311.

Figure 21:
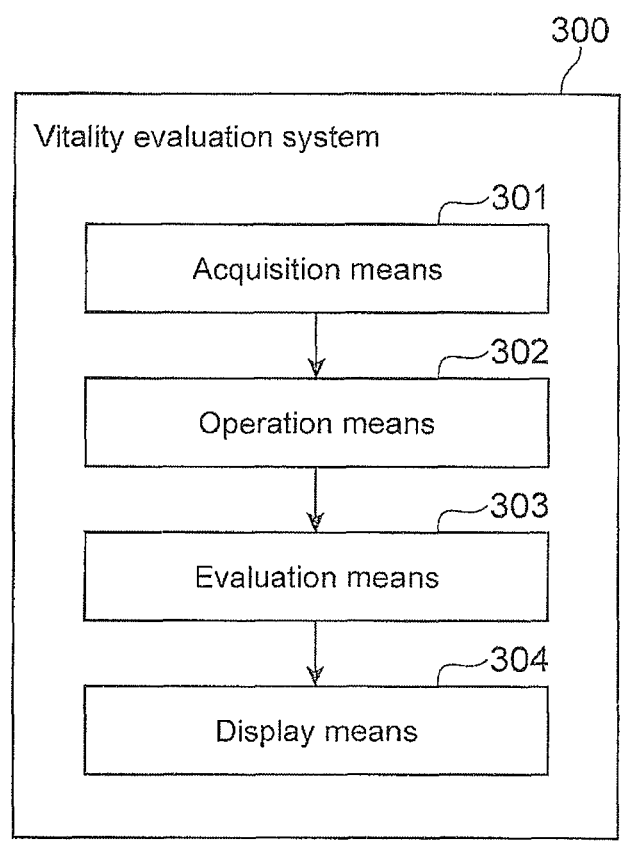
FIG. 21 is an outline diagram of the functional arrangement of the vitality evaluation system.

As shown in FIG. 21, the vitality evaluation system 300 includes, as functional components, an acquisition means 301, an operation means 302, an evaluation means 303, and a display means 304.

The acquisition means 301 acquires delayed luminescence amount data on a leaf of a plant. The operation means 302 processes the acquired delayed luminescence amount data to calculate an index value. The evaluation means 303 compares the index value thus obtained and a predetermined threshold to evaluate vitality of the plant. The display means 304 displays the obtained evaluation result to a user.

The operation means 302 calculates, as the index value, a value obtained by one or more operating methods selected from the group consisting of the following (A), (B), and (C).

(A) A method using, as the index value, the delayed luminescence amount data after the elapse of a fixed preset time after excitation light irradiation.

(B) A method using, as the index value, a value represented by any of the following (1), (2), and (3).

$$D_{x1}/D_{x2} \quad (1)$$

$$D_{x1}-D_{x2} \quad (2)$$

$$(D_{x1}-D_{x2})/(D_{x1}+D_{x2}) \quad (3)$$

[In the formulae (1), (2), and (3), $D_{x1}$ represents the delayed luminescence amount at x seconds after excitation light irradiation and $D_{x2}$ represents the delayed luminescence amount at y seconds after excitation light irradiation. Here, x and y are positive real numbers and x≠y.]

(C) A method using, as the index value, at least one value selected from the group consisting of constants in a curve approximation formula approximating a relationship between elapsed time X after excitation light irradiation and the corresponding delayed luminescence amount Y.

As the index value in (C) above, one or more values selected from the group consisting of a, b, c, d, e, and λ in the following formulae (4), (5), and (6) may be used.

$$Y=a \cdot b^X \quad (4)$$

$$Y=a \cdot e^{(-\lambda \cdot X)} \quad (5)$$

$$Y=c+d \cdot X+e \cdot X^2 \quad (6)$$

[In the formulae (4), (5), and (6), X and Y are the elapsed time X after excitation light irradiation in the preset time domain and the corresponding delayed luminescence amount Y.]

The operation means 302 may perform any single operation method or may perform two or more operation methods selected from the group consisting of (A), (B), and (C).

The evaluation means 303 evaluates the vitality of the plant by comparing the index value obtained by the operation means 302 and a predetermined threshold. As a processing method for comparing the index value and the threshold, a method among the methods of (i) to (iii) in the evaluation method described above may be used.

The predetermined threshold used in the evaluation means 303 may be one that is preset. The preset threshold may differ according to such conditions as plant species, region in which the plant grows, etc., and a plurality of those thresholds may be set. The most appropriate threshold may be selected at the time of evaluation in accordance with the conditions, such as the species of plant subject to evaluation, the region in which the plant grows, etc.

The vitality evaluation system 300 may further have an input means (not shown). The input means inputs a vitality index of the plant. The vitality index of the plant may, for example, be the terminal branch growth increment, the xylem pressure potential, or a vitality evaluation rank according to expert or another growth index. If evaluation of acute stress is the purpose, the vitality index is preferably a water potential (xylem pressure potential). Cr, if evaluation of chronic stress is the purpose, the vitality index is preferably a branch growth increment, a trunk growth increment, or a vitality evaluation rank according to expert. As the branch growth increment, for example, the branch growth increment of a terminal branch in the current year may be used. A plurality of types of vitality indices may be used. If the vitality system 300 has the input means, the operation means 302 may further calculate correlation coefficients of index values calculated by two or more operation methods selected from the group consisting of (A), (B), and (C) above and the input vitality index, and determine the operation method that exhibits the highest correlation coefficient. The display means 304 may display the determined operation method to the user.

The operation means 302 preferably calculates index values by all of the operation methods (A), (B), and (C). The optimal operation method of the highest correlation coefficient may be determined according to each condition, such as the species of plant subject to evaluation, the region in which the plant grows, etc. Once the operation method that is optimal for the plant subject to evaluation has been determined, the user may use this method in subsequent evaluations to perform vitality evaluation of the plant. Also, the user may determine the threshold at the time of evaluation in accordance with the condition, such as the type of vitality index of the plant, the species of plant, the region in which the plant grows, etc. Once the threshold has been determined, the threshold may be used as the predetermined threshold in subsequent evaluations.

The vitality evaluation system 300 may further include the measurement system described above. In this case, the vitality evaluation system 300 may further include a data transfer means. The data transfer means outputs the delayed luminescence amount data obtained by the measurement system and inputs the delayed luminescence amount data into the acquisition means 301. The measurement system may further have the recording unit recording the chlorophyll amount data. In this case, the operation means 302 may calculate corrected delayed luminescence amount data by correcting the delayed luminescence amount data by the chlorophyll amount per specific area and use the corrected delayed luminescence amount data in place of the delayed luminescence amount data.

The present invention may also be implemented as in the following embodiment.

[Method for Selecting a Plant Based on Vitality Evaluation]

A method for selecting a plant based on vitality evaluation according to the present embodiment (may also be referred to hereinafter simply as "selection method") includes (a) a step of obtaining data of a predetermined delayed luminescence amount and (b) a step of processing a plurality of the data items obtained to select an individual plant of good growth or poor growth.

In the (a) step of acquiring the data of the specific delayed luminescence amount, the delayed luminescence of a leaf is measured for each plant of a group of plants subject to selection to obtain the data of the delayed luminescence amount in a time domain in which the delayed luminescence amount increases when the xylem pressure potential is decreased.

As examples of the group of plants subject to selection, a group of plants growing in a certain region, a group of plants of the same species growing in a fixed growth environment, such as street trees planted at a specific interval, etc., can be cited.

The data of the delayed luminescence amount acquired in step (a) are data in the time domain in which the delayed luminescence amount increases when the xylem pressure potential is decreased (may also be referred to hereinafter as "time domain A"). For example, in a case of a delayed luminescence pattern of a leaf of Japanese mountain cherry that is observed while changing the xylem pressure potential as shown in FIG. 1, the time domain in which the delayed luminescence amount increases when the xylem pressure potential is decreased is the domain of (A). This time domain A differs according to the species of plant. The time domain A unique to the plant can be determined according to the species of plant by changing the xylem pressure potential. Also, a more optimal time domain A may be set in reference to results of prior measurement of a sample group that is clearly being stressed and a sample group that can be judged to be growing appropriately.

The data of the delayed luminescence amount acquired in step (a) suffice to be data acquired in the time domain A and, for example, may be data of the delayed luminescence amount at a predetermined point within the time domain A (for example, at 0.4 seconds) or may be cumulative data of delayed luminescence amounts measured in a predetermined time interval within the time domain A (for example, an interval of 0.1 second to 2 seconds).

The data of the delayed luminescence amount acquired in step (a) are preferably data within a time domain in which an absolute value of a correlation coefficient of leaf water potential and the delayed luminescence amount is greater than an absolute value of a correlation coefficient of the leaf water potential and chlorophyll fluorescence (Fv/Fm) (may also be referred to hereinafter as "time domain B"). For example, as shown in FIG. 2, the absolute value of the correlation coefficient of the leaf water potential and the delayed luminescence amount takes on a maximum value at an initial stage of measurement. In the vicinity of the maximum value, the absolute value of the correlation coefficient is greater than the absolute value of the correlation coefficient of the leaf water potential and the chlorophyll fluorescence (Fv/Fm) as shall be described below in regard to an example. The chlorophyll fluorescence (Fv/Fm) may be measured by a conventional method. For example, it may be measured by a pulse-modulated chlorophyll fluorescence measurement apparatus (for example, FluorPen100, made by Photon Systems Instruments). Fm is a maximum value of fluorescence intensity, Fo is a minimum value of fluorescence intensity, and Fv is Fm minus Fo. Fv/Fin represents a maximum yield of photosynthesis and is generally known to take a value of approximately 0.80 to 0.83 under optimal conditions in higher plants (see Kintake Sonoike, Methods for Photosynthesis Research (Chapter 4 Spectroscopic Measurement Part 3 Pulse-Modulated Fluorescence), Low Temperature Science, vol. 67, 2008, coedited by The Institute of Low Temperature Science, Hokkaido University and The Japanese Society of Photosynthesis Research, p. 507).

The time domain B differs according to the species of plant. The time domain B unique to the plant can be determined according to the species of plant by comparing the absolute value of the correlation coefficient of the leaf water potential and the delayed luminescence amount and the absolute value of the correlation coefficient of the leaf water potential and the chlorophyll fluorescence (Fv/Fm).

The time domain B may, for example, be the time domain of 0.01 second to 5 seconds after excitation light irradiation. The data of the delayed luminescence amount in the time domain B may, for example, be data of the delayed luminescence amount at a predetermined point within the time domain B (for example, at 0.4 seconds) or may be cumulative data of delayed luminescence amounts measured in a predetermined time interval within the time domain B (for example, an interval of 0.1 second to 5 seconds). The time domain B may, for example, be a time domain of 0.05 seconds to 4 seconds after excitation light irradiation, a time domain of 0.1 second to 3 seconds after excitation light irradiation, or a time domain of 0.1 second to 2 seconds after excitation light irradiation. Also, the time domain B is preferably a time domain of ±1 second, more preferably a time domain of ±0.5 seconds, and even more preferably a time domain of ±0.1 second centered at a time at which the maximum value is exhibited.

A leaf collected from the plant may be used or a leaf growing on the plant may be used directly in measuring the delayed luminescence.

Although the temperature condition of the delayed luminescence measurement is not restricted in particular as long as it is fixed during the measurement, it is preferably 5 to 35° C. and more preferably 20 to 30° C.

The delayed luminescence measurement may be performed by a known apparatus and method, for example, the apparatus and method described in WO2005/062027. As a more predetermined example, a method of performing a dark treatment followed by excitation light irradiation on a leaf of the plant and thereafter measuring the weak luminescence emitted by the leaf of the plant under a dark condition can be cited.

The duration of performing the dark treatment on the leaf of the plant is preferably 5 to 1200 seconds and more preferably 150 to 600 seconds.

The wavelength of the excitation light irradiated onto the leaf of the plant is preferably 280 to 900 nm and more preferably 400 to 750 nm.

The duration of irradiation of the excitation light onto the leaf of the plant is preferably 0.1 to 60 seconds and more preferably 0.5 to 20 seconds.

In measuring the delayed luminescence, the area of the leaf exposed to a delayed luminescence detector is preferably a predetermined area. The predetermined area, although not restricted in particular, is preferably 0.15 to 80 $cm^2$ and more preferably 0.5 to 10 $cm^2$.

In the (b) step of processing the plurality of the data items obtained to select an individual plant of good growth or poor growth, the data of the plurality of delayed luminescence amounts obtained are processed to select a plant exhibiting a delayed luminescence amount not less than a preset upper limit threshold as an individual of poor growth or select a plant exhibiting a delayed luminescence amount not more than a preset lower limit threshold as an individual of good growth.

As mentioned above, the delayed luminescence amount obtained in step (a) is negatively correlated with the leaf water potential. That is, when the delayed luminescence amount is high, the leaf water potential is low, and oppositely when the delayed luminescence amount is low, the leaf water potential is high. Therefore, in the group of plants subject to selection, an individual (group) of high delayed luminescence amount tends to be poor in growth state and an individual (group) of low delayed luminescence amount tends to be good in growth state.

From such a standpoint, the method for processing (analyzing) the data of the delayed luminescence amounts is not restricted as long as it is a method by which an individual plant with the delayed luminescence amount being not less than the preset upper limit threshold or an individual plant with the delayed luminescence amount being not more than the preset lower limit threshold can be identified. The upper limit threshold and the lower limit threshold are set as suited in accordance with the data processing (analyzing) method, the purpose of selection, etc.

Examples of methods for processing (analyzing) the data of the delayed luminescence amounts to select individual plants include but are not restricted to the following methods of (i) to (iii).

(i) Ranking

The data are ranked based on the delayed luminescence amount and individual plants within a range of the top X % (for example, the top 10% when ranking is performed in the order of decreasing delayed luminescence amount) or the bottom X % (for example, the bottom 10% when ranking is performed in the order of decreasing delayed luminescence amount) are identified and selected. For example, if ranking is performed in the order of decreasing delayed luminescence amount, the top 10% can be identified and selected as individual plants of poor growth. Or, the bottom 10% can be identified and selected as individual plants of good growth. The upper limit threshold and the lower limit threshold in this case are the top 10% and the bottom 10%, respectively. With this method, a predetermined number of samples is always selected, and therefore the method is effective in a case where a predetermined number of samples of good growth or poor growth are to be identified in a forest or farm, such as in cases of thinning or culling or in cases where saplings, mature trees, or crops of good growth are to be selected as commodities.

(ii) Use of a Normal Distribution

The data of a population are assumed to follow a normal distribution and a Y % prediction, interval (the range for which the prediction of which range the sample values to be observed in the future will fall within is performed) is calculated. If the measured values so far do not fall within the Y % prediction interval, the individual plant is identified and selected as being an individual of good or poor growth. For example, when Y=80, the ranges at the respective ends outside the prediction interval are respectively 10%, and if the measured values so far do not fall within the 80% prediction interval, the sample can be identified and selected as being of good growth (top 10%) or poor growth (bottom 10%).

(iii) Use of a Bootstrap Method

By a bootstrap method (a method in which sampling with replacement is performed repeatedly on a single sample to generate a large quantity of samples and an estimate value is calculated from the samples thus generated to analyze a property of a population, an error of estimation by a model, etc.), respective confidence intervals (for example, 95% confidence intervals) of a $Z_1$ percentile value (for example, a 10 percentile value) and a $Z_2$ percentile value (for example, a 90 percentile value) of the population are estimated. If the measured values so far do not fall within an interval sandwiched by the confidence interval of the $Z_1$ percentile value and the confidence interval of the $Z_2$ percentile value, the sample is identified and selected as being of good growth (top 10%) or poor growth (bottom 10%).

With the method of (iii), individual plants of good growth or poor growth may be identified while including the individuals within the 95% confidence interval of the 10 percentile value (or the 90 percentile value) (range indicated by an arrow A in FIG. 3) or individual plants of good growth or poor growth may be identified without including the individuals within the 95% confidence interval of the 10 percentile value (or the 90 percentile value) (range indicated by an arrow B in FIG. 3).

With the methods of (ii) and (iii), the number of individual plants that are selected as being of good or poor growth changes depending on the measured sample group because good or poor growth is identified while taking into consideration the variation of data. Then, the characteristics of the group can be examined from the variation of data. This is effective, for example, if the growth state of the plants in a certain region is to be characterized at the same time.

With the methods of (i), (ii), and (iii), any two may be used in combination or all three may be used in combination. By selecting the individual plants that are identified as being of good or poor growth by all of the methods used in combination, it becomes possible to select individuals that are more significantly good or poor in growth.

The vitality of a plant decreases upon receiving the influence of stress. Drought, high temperature, freezing, oligotrophy, deficiency of microelements, salt damage, disease and insect damage, etc., can be cited as examples of stress. With the selection method according to the present embodiment, the vitality is preferably that which reflects the influence of drought stress.

The selection method according to the present embodiment may further include (c) a step of measuring a chlorophyll amount of the plant leaf to obtain chlorophyll amount data and (d) a step of calculating data of corrected delayed luminescence amount by correcting the data of delayed luminescence amount obtained in step (a) by the chlorophyll amount per predetermined area. In a case where the step (c) and the step (d) are included, it is preferable to use the data of the corrected delayed luminescence amounts in place of the data of the delayed luminescence amounts in step (h).

In step (c), the chlorophyll amount in the plant leaf is measured to acquire the chlorophyll amount data.

The method for measuring the chlorophyll amount is not restricted in particular as long as it is a known method, and a method using reflected light obtained by irradiating light onto the plant leaf as described in JP2011-38879 or a method using transmitted light obtained, by irradiating light onto the plant leaf as implemented in the SPAR-502 Chlorophyll Meter (made by Konica Minolta, Inc.) is preferably used.

In a case of measuring the chlorophyll amount using reflected light or transmitted light, the area of the leaf exposed to a detector of reflected light or transmitted light is preferably a predetermined area. Step (d) can thereby be performed more simply. The predetermined area is not restricted in particular but is preferably 0.06 to 80 cm² and more preferably 0.5 to 10 cm².

In step (d), the data of the delayed luminescence amount obtained in step (a) are corrected by the chlorophyll amount per predetermined area to calculate the data of the corrected delayed luminescence amount.

The data of the corrected delayed luminescence amount are obtained, for example, by division by the chlorophyll amount per predetermined area of the plant leaf. The data (S) of the corrected delayed luminescence amount may also be calculated by the following formula.

$$S = \left(\frac{T \times e - f}{U \times g - h}\right) \quad \text{[Numerical Formula 2]}$$

T: Delayed luminescence amount
U: Chlorophyll amount per predetermined area
e, g: Weighting of the delayed luminescence amount and chlorophyll amount values
f, h: Baselines of the measured value of the delayed luminescence and the measured value of the chlorophyll amount

[Measurement System]

A measurement system for evaluating vitality of a plant according to the present embodiment (may also be referred to hereinafter simply as "measurement system") comprises at least a dark treatment tool and a measurement apparatus. Preferably, there are pluralities of the dark treatment tools.

The dark treatment tool has an opening capable of being opened and closed and shades a portion or all of a leaf of a plant. The dark treatment tool is preferably arranged so that the dark treatment can be performed on a portion or all of an individual leaf of a plant without cutting the individual leaf of the plant. The opening capable of being opened and closed may, for example, be a shutter mechanism.

FIG. 13 is a schematic view of the dark treatment tool according to the embodiment. FIGS. 14 and 15 show explanatory diagrams of methods for using the dark treatment tool shown in FIG. 13.

The dark treatment tool 100 shown in FIG. 13 has the main body portion 20 and the shutter opening 10 arranged from a lightweight shutter mechanism. The dark treatment tool 100 covers and shades a portion or all of an individual leaf by means of the main body portion 20. The main body portion 20 is formed of a material of high shading property. Resin plates, thin metal plates of light weight, and plates made of paper or wood can be cited as examples of the material forming the main body portion 20. It is further preferable for these materials to be coated in black so as not to allow passage of external light. Further, a material, having a shading property and yet being flexible to enable close contact with the plant surface to be achieved while avoiding damaging of the plant, is preferably used for the entirety of the inner surfaces of the main body portion 20 that sandwich a leaf or a periphery of the shutter opening 10 corresponding to a measured portion of the leaf. This can be realized, for example, by using foamed urethane or a rubber material and further disposing packings of similar material so as to surround the measured portion or arranging multiple packings in the form of pleats or further forming a maze-like structure with the same material to increase the shading property.

As shown in FIG. 14, the dark treatment tool 100 is used by folding the main body portion 20 so as to cover a portion (FIG. 14A) or all (FIG. 14B) of an individual leaf. After folding the main body portion 20, the end portion 21 of the main body portion 20 may be folded back and fixed. In this process, the shutter opening 10 is positioned at the measured portion of the individual leaf.

As shown in FIG. 15, to hold the dark treatment tool 100 at an individual leaf of a tree, the jigs 30 and 31 (FIGS. 15A and 15B) to be fastened to a branch or trunk or the jigs 30 and 32 (FIGS. 15B and 15C) fixed to the ground may further be included.

After performing the dark treatment by shading the individual leaf with the dark treatment tool 100 (for example, for 300 seconds), a light collecting unit of the measurement apparatus and the shutter opening 10 are connected to perform measurement of delayed luminescence. Preferably, a plurality of the dark treatment tools 100 are prepared apart from the measurement apparatus. Dark treatment of an individual leaf to be subject to measurement subsequently can thereby be performed while measuring the delayed luminescence with the measurement apparatus and significant reduction of measurement time is made possible because measurement of the subsequent individual leaf can be started immediately after the end of measurement of a certain individual leaf.

The measurement apparatus has the light collecting unit capable of being attached to and detached from the opening of the dark treatment tool, a light source unit arranged to irradiate light onto the plant leaf, and a delayed luminescence detecting unit detecting the delayed luminescence of the plant leaf resulting from the light irradiated by the light source unit. The light collecting unit and the delayed luminescence detecting unit may be integral or may be separated as shall be described below.

FIG. 16 shows explanatory diagrams of the method for using the measurement system according to the embodiment. FIG. 17 is a schematic view of the measurement apparatus according to the embodiment. FIG. 18 shows schematic views of a plurality of embodiments of measurement apparatuses. FIG. 19 shows schematic views of the measurement apparatus according to the embodiment.

The measurement system shown in FIG. 16A comprises the dark treatment tool 100 and the measurement apparatus 200. The measurement apparatus 200 has the light collecting unit 50, the light source unit 60 disposed in the light collecting unit 50, and the delayed luminescence detecting unit 80. It may also have a recording unit recording the data measured by the delayed luminescence detecting unit 80, an operating unit processing the measured data, an input unit inputting a processing method, and a control unit controlling actions of the light source unit 60, the delayed luminescence detecting unit 80, etc. As the recording unit, the operating unit, the input unit, and the control unit, a computer having the functions of these units may be used. The computer may be incorporated inside the measurement apparatus 200 or may be connected from the exterior.

The light collecting unit 50 is arranged to be connected to the shutter opening 10 of the dark treatment tool 100 and, after connection, the arrangement can be regarded as being an integral measurement apparatus without leakage of light that influences measurement (see FIG. 16B). A state enabling measurement is entered by connecting the light collecting unit 50 and the shutter opening 10 and opening the shutter. In this process, the shutter may be opened manually by a measurer or a mechanism that opens the shutter automatically upon connection may be included (see FIG. 16C and FIG. 16D). In the state where the shutter is opened, only a predetermined shape and area of the leaf are exposed.

The light collecting unit 50 includes an excitation light source (light source unit 60) for making the delayed luminescence be emitted. The light source unit 60 is arranged from a single or plurality of light sources capable of irradiating a plurality of wavelengths. That is, it is a multiple wavelength light source, such as a halogen lamp, or an arrangement combining a wavelength selection filter with such a light source, or an assembly of LEDs of different peak wavelengths, etc.

The light source unit 60 irradiates light of specific wavelength onto the individual leaf. The wavelength is 400 nm to 1000 nm. Here, the light source unit 60 may be a monochromatic light source or a light source combining a plurality of light sources. The light emission by the light source unit 60 may be continuous for a predetermined duration or pulse lighting may be performed in any pattern. A plurality of light sources having the same or different wavelength characteristics may be made to emit light successively or the plurality of light sources may be made to emit light simultaneously. Also, a shutter that opens and closes in synchronization with the turning on and turning off of the light source may be combined to cut the afterglow of the light source.

As shown in FIG. 17 and FIG. 18, the leaf is excited by the light irradiated from the light source unit 60 and the delayed luminescence emitted from the leaf is guided to the photodetector 85 disposed in the delayed luminescence detecting unit 80. To transmit the delayed luminescence to the photodetector 85 efficiently in this process, the light collecting lens 55 may be included or the optical fiber or relay optical system 70 capable of relaying the delayed luminescence over a long distance may be used. By adopting the optical fiber or relay optical system 70 capable of relaying the delayed luminescence over a long distance, the light collecting unit 50 and the delayed luminescence detecting unit 80 are made separable to enable the light collecting unit 50 to be made compact and lightweight and thereby enable the work of measuring upon coupling to the dark treatment tool 100 attached to the individual leaf to be performed more efficiently.

As the photodetector 85 disposed in the delayed luminescence detecting unit 80, a photomultiplier tube, an avalanche photodiode, a silicon photodiode, etc., may be used. The shutter 81 for preventing the entry of excitation light may be disposed in front of the photodetector 85 (see FIGS. 18A and 18B). Also, the shutter may be omitted by performing control so that the photodetector 85 does not receive light during excitation light irradiation (see FIG. 18C).

The condenser lens 82 may further be disposed in front of the photodetector 85 to improve the light collecting efficiency (see FIG. 18A). Positioning of the condenser lens 82 is effective in the case where the optical fiber or relay optical system 70 is used.

As shown in FIG. 19, the delayed luminescence detecting unit 80 may have the display unit 83, arranged to display information during measurement, and the input unit 84 with a button, etc., arranged to operate the measurement apparatus (see FIG. 19A). If the measurement apparatus is compact and lightweight so as to be portable, the measurer can be outfit with the apparatus and can make measurements while moving. For this purpose, a belt or strap for outfitting may be mounted on the light collecting unit or the detecting unit (see FIG. 19B).

The measurement apparatus may have a mechanism that outputs a message indicating that data are insufficient until data of enough amounts enabling identification are collected with high reliability and accuracy.

In addition to the above arrangement, the measurement apparatus may further have a photodetecting unit detecting light that arises as a result of the light irradiated by the light source unit and reflects the chlorophyll amount in the plant leaf, and a recording unit recording the data of the delayed luminescence amount corresponding to the delayed luminescence detected by the delayed luminescence detecting unit and recording chlorophyll amount data corresponding to the light reflecting the chlorophyll amount and detected by the photodetecting unit. The photodetecting unit and the recording unit may be apparatuses that are independent of the measurement apparatus.

By the above-described dark treatment tools, which enable the dark treatment to be performed on a plurality of leaves in advance, and the compact, lightweight measurement apparatus that is portable, delayed luminescence measurement can be performed in a short time without cutting the individual leaf of the plant and a problem of individual differences arising due to the cutting of the leaf can be resolved.

EXAMPLES

The present invention shall now be described in further detail by way of examples. However, the present invention is not restricted to these examples.

Example 1

Acute Drought Stress Application Test

[Method for Performing Acute Drought Stress Application Test on an Individual Leaf]

A leaf of a subject plant, watered sufficiently once a day, was collected and immediately transported into a laboratory under wet and dark conditions and measurement was performed in accordance with the following protocol. First, the leaf was placed in a pressure chamber (trade name: DIK-7000; made by Daiki Rika Kogyo Co., Ltd.) and the xylem pressure potential in the natural state was measured using high-pressure nitrogen gas. The osmotic potential is close to 0 and the xylem pressure potential was thus deemed to be the water potential. Next, the leaf was placed in a weak luminescence measurement apparatus (Type 6100A Leaf Adapter with Mask, made by Hamamatsu Photonics K. K.) and after performing a dark treatment for 300 seconds and then irradiating excitation light (680 nm, 10 µmol/m$^2$/s) for 10 seconds, weak luminescence was measured for 400 seconds under a dark condition. The area of the leaf exposed to the detector in this process was set so that two circular portions of 7 mm diameter were exposed symmetrically across a central leaf vein (main leaf vein) of the leaf. Thereafter, the chlorophyll fluorescence (Fv/Fm), evapotranspiration rate (ET), chlorophyll meter value (SPAD), and spectral reflectivity were measured successively. The Fv/Fm was measured by a pulse-modulated chlorophyll fluorescence measurement apparatus (FluorPen100, made by Photon Systems Instruments). The evapotranspiration rate was measured by the AP4 Porometer (made by Delta-T Devices Ltd.), the chlorophyll meter value was measured by the SPAD-502 Chlorophyll Meter (made by Konica Minolta, Inc.), and the spectral reflectivity was measured by the FieldSpec Hand-Held spectroreflectometer with dedicated Leaf Clip (made by Analytical Spectral Devices Inc.). Measurements were similarly made in accordance with the above protocol upon dehydrating in the pressure chamber until the xylem pressure potential became −2.0 MPa or −3.0 MPa. The measurements were repeated on a total of 30 leaves collected by collecting 3 leaves from each of 10 individual plants.

As the subject plants, outdoor-planted trees of Japanese mountain cherry and Japanese camellia and potted young plants of camphor tree, Japanese mountain cherry, Yoshino cherry, Kousa dogwood, and tomato, all of good growth, were used. With the outdoor-planted tree of Japanese mountain cherry, tests were performed in 2011, a year before tests were performed on the other subject plants (in 2012), by repeating measurements on a total of 60 leaves with only the dehydration to −3.0 MPa in the pressure chamber being performed and the dehydration to −2.0 MPa not being performed (the results for this tree shall be indicated hereinafter by "Japanese mountain cherry 2011"). Also, with the tomato, the weak luminescence measurement time was set to 150 seconds, the dehydration in the pressure chamber was performed to −1.5 MPa, and measurements were repeated on a total of 32 leaves collected by collecting 2 or 3 leaves from 15 individual plants.

[Method for Performing Acute Drought Stress Application Test on Potted Young Plants]

Twenty eight individual potted young plants of Japanese mountain cherry were prepared, watering was performed once a day at around 4 o'clock in the morning by an automatic watering apparatus for 14 individual plants of a control group, watering was stopped for 14 individuals of a treated group, and measurements were made as follows at the 0th, 2nd, 5th, and 9th day after stoppage of watering. Leaves were collected from the respective individuals of the control group and the treated group and the leaves were placed in the pressure chamber (trade name: DIK-7000; made by Daiki Rika Kogyo Co., Ltd.) to measure the xylem pressure potential in the natural state using high-pressure nitrogen gas. Each leaf was placed in a weak luminescence measurement apparatus (Type 6100A Leaf Adapter with Mask, made by Hamamatsu Photonics K. K.) and after performing the dark treatment for 300 seconds and then irradiating excitation light (680 nm, 10 µmol/m$^2$/s) for 10 seconds, the weak luminescence was measured for 400 seconds under the dark condition. The area of the leaf exposed to the detector in this process was set so that two circular portions of 7 mm diameter were exposed symmetrically across a central leaf vein (main leaf vein) of the leaf. Thereafter, the chlorophyll fluorescence (Fv/Fm), chlorophyll meter value (SPAD), and spectral reflectivity were measured successively. These measurements were made by the apparatuses and methods described above. One individual in the control group was eliminated from being subject to analysis because damage due to whitefly was observed on the leaves during measurement, and therefore the number of individual plants subject to analysis was 27, consisting of 13 individuals of the control group and 14 individuals of the treated group.

[Results]

(Change of Delayed Luminescence Pattern Due to Drought Stress)

In comparison to the control group to which the drought stress was not applied, the delayed luminescence amount in a time domain at an initial stage of measurement was increased in the stress group to which the drought stress was applied to the leaf of the subject plant. As an example, the changes with time of the delayed luminescence amount (may also be referred to as the "delayed luminescence pattern") of leaves of Japanese mountain cherry in a control group and stress groups (low stress: xylem pressure potential of −2.0 MPa; high stress: xylem pressure potential of −3.0 MPa) are shown in FIG. 1. It can be understood that with the stress groups with which the water potential was reduced by dehydration, the delayed luminescence amount is increased in comparison to that of the control group in a time domain at an initial stage of measurement, for example, at 0.7 seconds after. The delayed luminescence pattern changes due to drought stress and a point (cross point) occurs at which the delayed luminescence pattern of the control group and the delayed luminescence patterns of the stress groups intersect. With the stress groups, the delayed luminescence amount is increased in comparison to that of the control group in the time domain before the cross point and the delayed luminescence amount is decreased in comparison to that of the control group in the time domain after the cross point.

(Correlation Coefficient of Delayed Luminescence Amount and Water Potential)

FIG. 2 shows values of a correlation coefficient of the delayed luminescence amount and water potential at respective measurement times. In FIG. 2, the ordinate indicates the correlation coefficient (Pearson's correlation coefficient) of the delayed luminescence amount and the water potential of the leaf of the subject plant at each measurement time, and the abscissa indicates the measurement time. For data points at which the measured value was saturated, analysis was performed deeming that there were no data at just those data points. In regard to Japanese mountain cherry 2011, the values of the correlation coefficient of the delayed luminescence amount and the water potential at the respective measurement times are shown for the control group and the stress group of −3.0 MPa water potential, and results for Japanese mountain cherry X are also shown for comparison. The data of Japanese mountain cherry X are the data of Japanese mountain cherry after elimination of the data for the −2.0 MPa water potential. From FIG. 2, it can be understood that for all subject plants, the absolute value of the correlation coefficient increases from 0.1-2 seconds after the start of measurement (immediately after the end of irradiation of the excitation light) and the correlation with the water potential is high.

The times at which the absolute value of the correlation coefficient becomes the maximum for the respective subject plants are, for example, 1 second for Japanese mountain cherry, 0.4 seconds for camphor tree, 0.2 seconds for Japanese camellia, 1.4 seconds for Yoshino cherry, 0.5 seconds for Kousa dogwood, and 0.6 seconds for tomato (see FIG. 2).

The correlation coefficients of the delayed luminescence amount (DF), SPAD value, SPADIND, Fv/Fm, and evapotranspiration rate (ET) and the water potential are shown in Table 1. The SPADIND is a data item with which the SPAD in the stress state is replaced by the SPAD of the control group of the same sample.

TABLE 1

Correlation coefficient of the delayed luminescence amount and the water potential

| | SPAD | SPADIND | Fv/Fm | ET | DF (0.7 seconds) |
|---|---|---|---|---|---|
| Japanese mountain cherry | | | | | |
| Correlation coefficient with respect to the water potential | −0.252 | −0.095 | 0.383 | 0.376 | −0.647 |
| Camphor tree | | | | | |
| Correlation coefficient with respect to the water potential | −0.282 | 0.013 | 0.686 | 0.040 | −0.806 |
| Japanese camellia | | | | | |
| Correlation coefficient with respect to the water potential | −0.099 | −0.002 | 0.154 | 0.429 | −0.651 |
| Yoshino cherry | | | | | |
| Correlation coefficient with respect to the water potential | −0.122 | 0.035 | 0.311 | 0.424 | −0.733 |
| Kousa dogwood | | | | | |
| Correlation coefficient with respect to the water potential | −0.116 | −0.022 | 0.39 | 0.312 | −0.640 |
| Tomato | | | | | |
| Correlation coefficient with respect to the water potential | −0.311 | 0.025 | 0.411 | 0.685 | −0.659 |
| Japanese mountain cherry 2011 | | | | | |
| Correlation coefficient with respect to the water potential | −0.391 | −0.004 | 0.126 | 0.583 | −0.847 |

TABLE 1-continued

Correlation coefficient of the delayed luminescence amount and the water potential

| | SPAD | SPADIND | Fv/Fm | ET | DF (0.7 seconds) |
|---|---|---|---|---|---|
| Japanese mountain cherry (potted young plants) | | | | | |
| Correlation coefficient with respect to the water potential | −0.079 | — | 0.555 | 0.003 | −0.613 |

In regard to the correlation coefficient of the delayed luminescence amount and the water potential in FIG. 1, the values for the delayed luminescence amount at 0.3 seconds after or 0.7 seconds after the start of measurement (immediately after the end of excitation light measurement) are used. It can be understood that the delayed luminescence amount is high in absolute value of the correlation coefficient with respect to the water potential in comparison to the correlation coefficients of the other variables and the water potential, and is comparatively strong in correlation with the water potential. In particular, that the delayed luminescence amount is stronger in correlation with the water potential than Fv/Fm, which is used as a general index that reflects the photosynthesis activity state, indicates that the delayed luminescence amount is effective for growth evaluation and photosynthesis research of plants.

(Selection of Samples from the Delayed Luminescence Amount Data)

In regard to the leaves of the plants subject to the [Method for performing acute drought stress application test on potted young plants] described above, the following three selection methods were used to identify samples of good and poor growths from the distribution of the delayed luminescence amount at 0.3 seconds after the start of measurement (immediately after the end of excitation light irradiation) of the stress group and the control group on the 5th day from the stoppage of watering.

Method 1. Identification by Ranking

The samples were ranked in the order of decreasing delayed luminescence amount and samples in the ranges of the top 10% and the bottom 10% were identified. The samples of the top 10% are samples of good growth and those of the bottom 10% are sample of poor growth.

Method 2. Identification by Calculation of a Prediction Interval Assuming a Normal Distribution The 80% prediction interval was calculated in assumption that the data of the population follow a normal distribution. In this case, the respective ends outside the prediction interval are respectively 10%, and if the measured values did not fall within the 80% prediction interval, the sample was identified as being of good growth (top 10%) or poor growth (bottom 10%).

Method 3. Identification by Calculation of Confidence Intervals by the Bootstrap Method The respective 95% confidence intervals for the 10 percentile value and the 90 percentile value of the population were estimated by the bootstrap method. If the measured values did not fall within the interval sandwiched by the 95% confidence interval for the 10 percentile value and the 95% confidence interval for the 90 percentile value, the sample was identified as being of good growth (top 10%) or poor growth (bottom 10%). In this process, an individual plant falling within a 95% confidence interval was identified by the following Method 3-1 or Method 3-2.

Method 3-1. Individual plants were identified to be of good growth or poor growth with the inclusion of the individuals within the 95% confidence interval of the 10 percentile value (or the 90 percentile value) (see FIG. 3).

Method 3-2. Individual plants were identified to be of good growth or poor growth without including the individuals within the 95% confidence interval of the 10 percentile value (or the 90 percentile value) (see FIG. 3).

The results of performing the above-described Method 1, Method 2, and Method 3 on the leaves of the subject plants to identify the top 10% and the bottom 10% from the distribution of the delayed luminescence amount at 0.3 seconds after the start of measurement (immediately after the end of excitation light irradiation) and identifying these respectively as being of good growth and poor growth are shown in Table 2. Good growth is indicated by o, poor growth is indicated by x, and a sample identified as being neither is indicated by an empty column. With Method 1, a predetermined number of good growth samples and poor growth samples were identified in accordance with the number of samples. With Method 2 and Method 3, the number of samples identified to be of good growth and the number of samples identified to be of poor growth differed in accordance with the delayed fluorescence amount distribution of the sample group. With Method 3-1, the ranges of good growth and poor growth are relatively wide and therefore there were samples within the control group that were identified as being poor in growth and samples within the stress group that were identified as being of good growth. Although the range of identification differs according to each method, samples that are significantly good or poor in growth are identified as being of good or poor growth in common by all methods.

TABLE 2

Identification of good growth individuals and poor growth individuals

| No. | DF (0.3 seconds) | Method 1 | Method 2 | Method 3-1 | Method 3-2 | |
|---|---|---|---|---|---|---|
| 1 | 121865 | | | o | | Control group |
| 2 | 237316 | | | x | | |
| 3 | 148207 | | | | | |
| 4 | 171648 | | | | | |
| 5 | 65938 | o | o | o | o | |
| 6 | 144786 | | | | | |
| 7 | 89578 | o | | o | | |
| 8 | 182732 | | | | | |
| 9 | 241849 | | | x | | |
| 10 | 96501 | o | | o | | |
| 11 | 114589 | | | o | | |
| 12 | 105431 | | | o | | |
| 13 | 213902 | | | | | |
| 14 | 149378 | | | | | Stress group |
| 15 | 160054 | | | | | |
| 16 | 229230 | | | x | | |
| 17 | 145930 | | | | | |
| 18 | 278510 | | | x | | |
| 19 | 206389 | | | | | |
| 20 | 466653 | x | x | x | x | |
| 21 | 116784 | | | o | | |
| 22 | 208845 | | | | | |
| 23 | 363414 | x | x | x | | |
| 24 | 129218 | | | | | |
| 25 | 191327 | | | | | |
| 26 | 217503 | | | | | |
| 27 | 348922 | x | x | x | | | o: good growth (top 10%);
x: poor growth (bottom 10%)

(Correlation Coefficients of Operated Values and the Water Potential)

Figure 7:
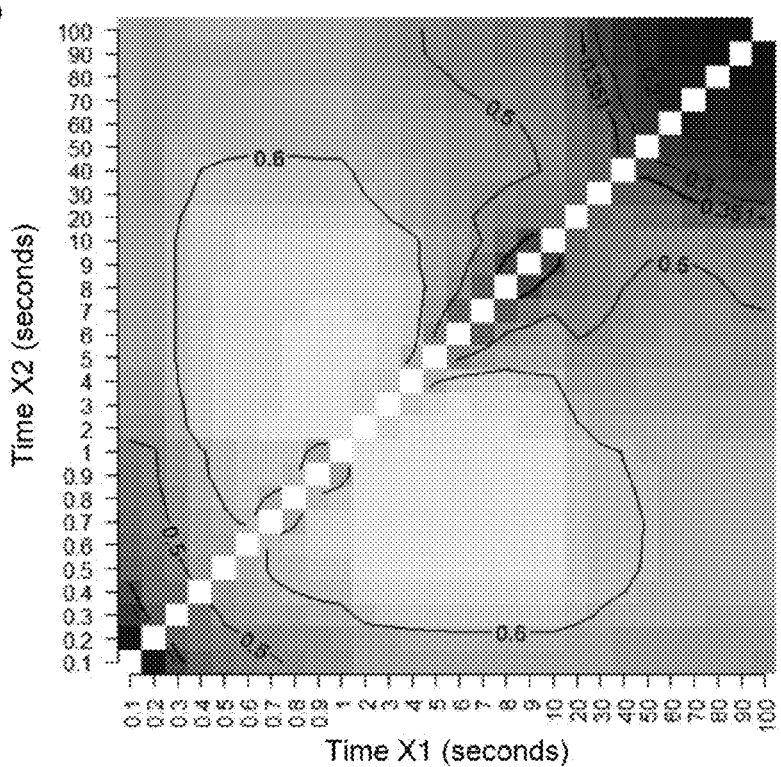
FIG. 7A is a graph of the absolute values of a correlation coefficient of a division type stress index and the water potential in Example 1.
FIG. 7B is a graph of the absolute values of a correlation coefficient of a subtraction type stress index and the water potential in Example 1.
Figure 7:
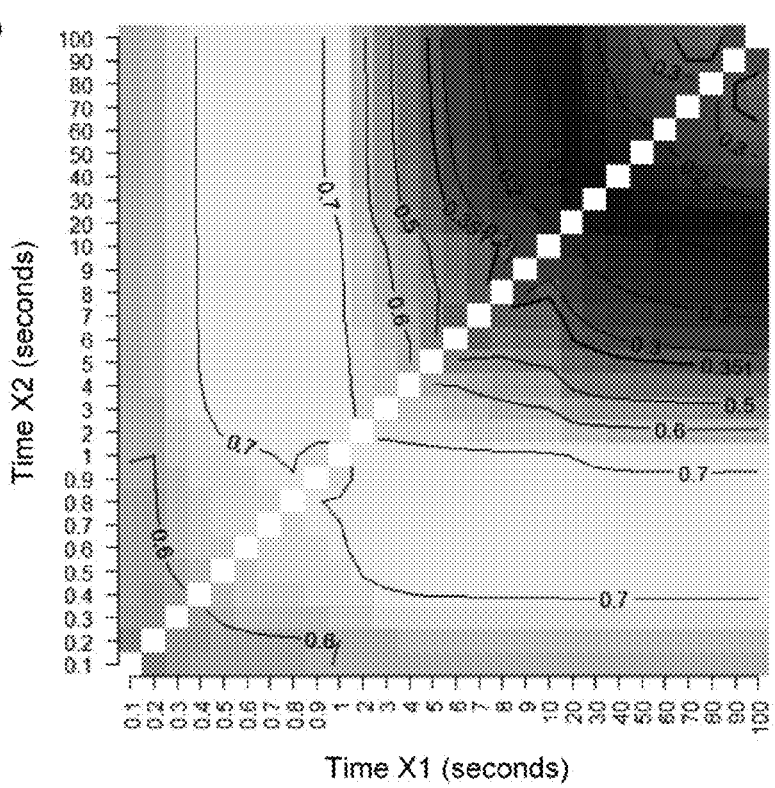
Figure 8:
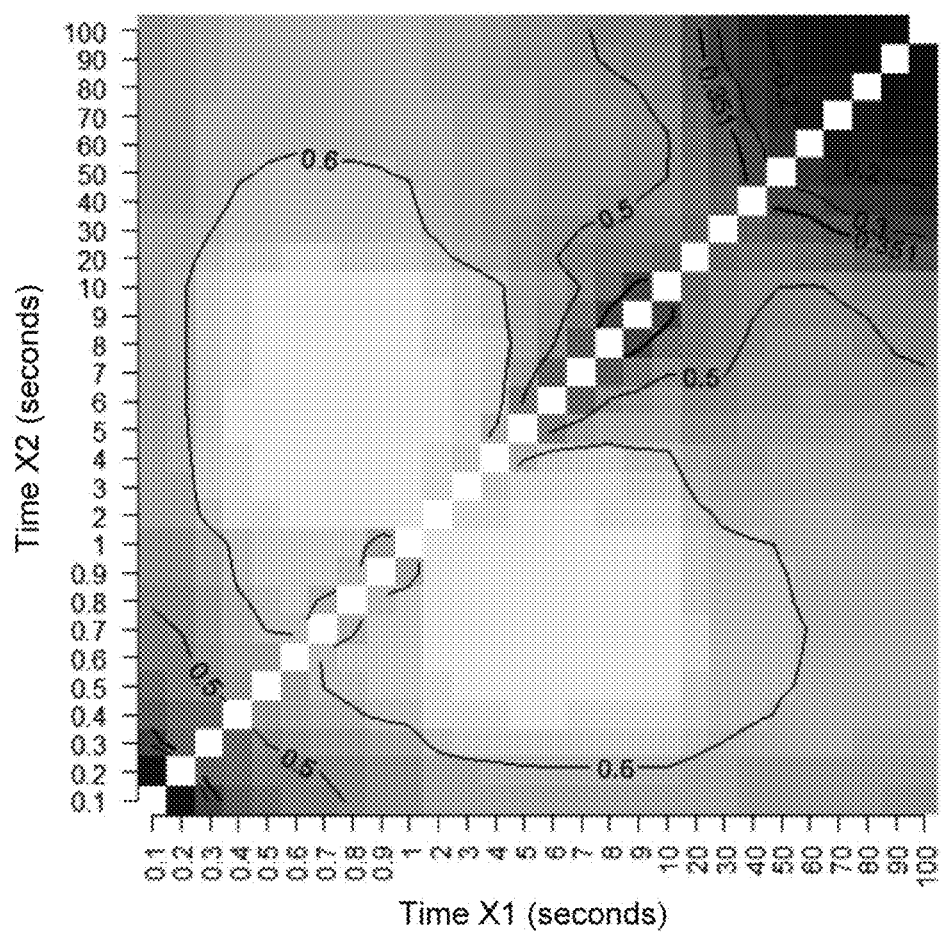
FIG. 8 is a graph of the absolute values of a correlation coefficient of a normalized difference type stress coefficient and the water potential in Example 1.
Figure 9:
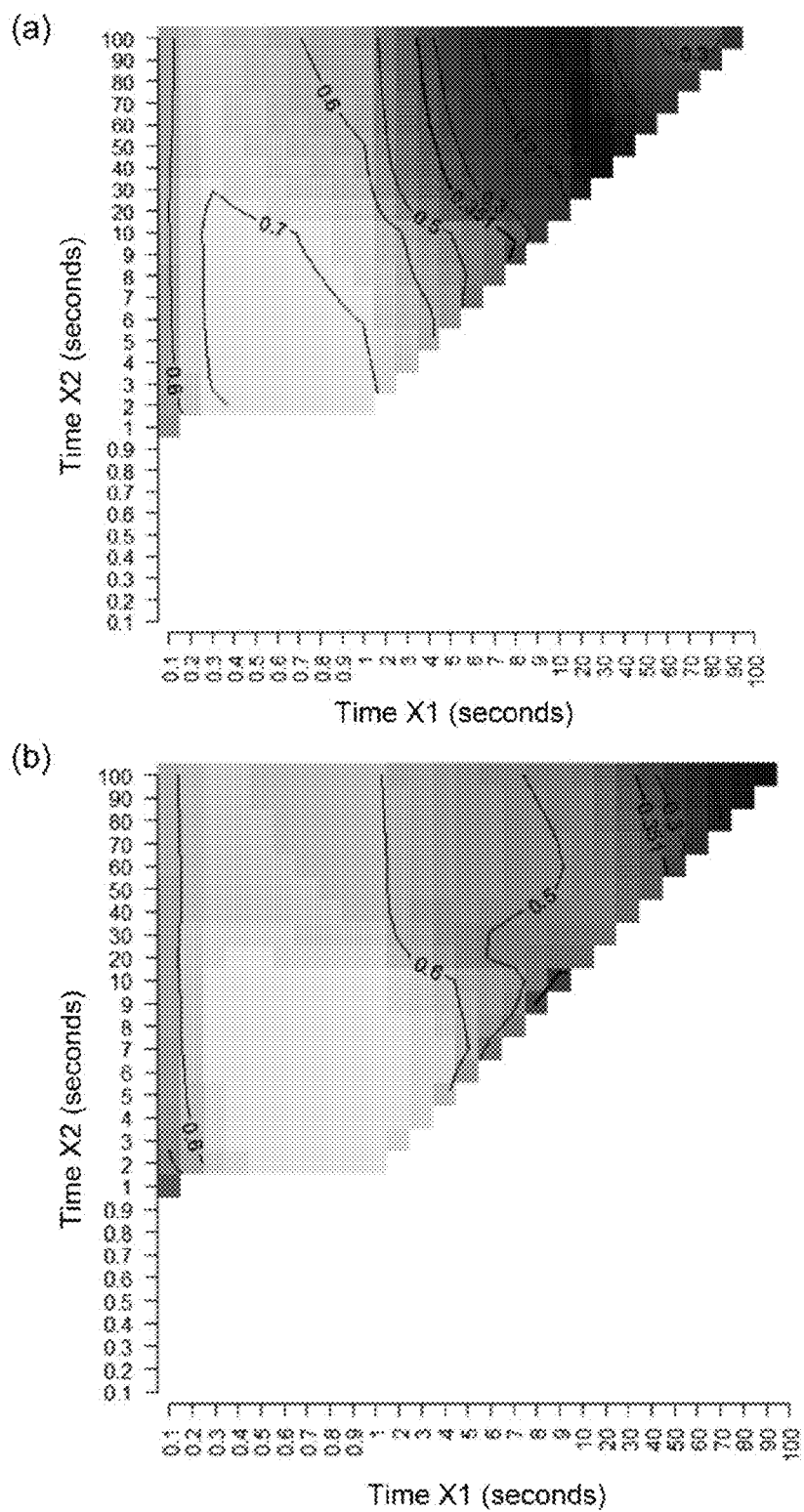
FIG. 9A is a graph of the absolute values of a correlation coefficient of a coefficient a of an exponential function expressed by a formula (4) and the water potential in Example 1.
FIG. 9B is a graph of the absolute values of a correlation coefficient of a coefficient b of the exponential function expressed by the formula (4) and the water potential in Example 1.

Correlation of operated values, obtained by using the delayed luminescence amount data at two measurement time points, and the water potential were examined. The operated values were obtained by using the delayed luminescence amount data obtained in Example 1 and performing the division type, subtraction type, and normalized difference type operations. Correlation coefficients of the operated values and the water potential were calculated. FIG. 7 and FIG. 8 show graphs of the absolute values of the correlation coefficients of the operated values, obtained by operations using the delayed luminescence amount data measured in Example 1, and the water potential. Each of the values shown in the graphs is an average value of the data of the seven types of plants besides the potted Japanese mountain cherry.

The absolute values of the correlation coefficient of the operated value O, obtained by the division type operation, that is, by the following formula (1), and the water potential are shown according to the measurement times in FIG. 7A. For each plant type, the measurement times for which the highest correlation coefficient value is obtained are shown together with the correlation coefficient value in Table 3.

$$O = D_{x1}/D_{x2} \quad (1)$$

TABLE 3

Correlation coefficient of the division type index of the delayed luminescence amount and the water potential

| | Optimal times for each type | | | | Times that are optimal in average for the data of the 7 types | | | | Difference with respect to the optimal times for the data of each type Difference of the absolute values of the correlation coefficient |
|---|---|---|---|---|---|---|---|---|---|
| | Correlation coefficient | Absolute value | X1 (s) | X2 (s) | Correlation coefficient | Absolute value | X1 (s) | X2 (s) | |
| Camphor tree | −0.850 | 0.850 | 0.8 | 3 | 0.829 | 0.829 | 2 | 1 | −0.021 |
| Yoshino cherry | −0.546 | 0.546 | 1 | 7 | 0.526 | 0.526 | 2 | 1 | −0.020 |

TABLE 3-continued

Correlation coefficient of the division type index of the delayed luminescence amount and the water potential

| | Optimal times for each type | | | | Times that are optimal in average for the data of the 7 types | | | | Difference with respect to the optimal times for the data of each type Difference of the absolute values of the correlation coefficient |
|---|---|---|---|---|---|---|---|---|---|
| | Correlation coefficient | Absolute value | X1 (s) | X2 (s) | Correlation coefficient | Absolute value | X1 (s) | X2 (s) | |
| Japanese camellia | 0.834 | 0.834 | 7 | 0.1 | 0.709 | 0.709 | 2 | 1 | −0.125 |
| Kousa dogwood | −0.682 | 0.682 | 0.9 | 4 | 0.664 | 0.664 | 2 | 1 | −0.018 |
| Japanese mountain cherry | −0.615 | 0.615 | 1 | 2 | 0.614 | 0.614 | 2 | 1 | −0.001 |
| 2011 Japanese mountain cherry 2011 | −0.890 | 0.890 | 0.6 | 2 | 0.876 | 0.876 | 2 | 1 | −0.014 |
| Tomato | −0.623 | 0.623 | 6 | 10 | 0.570 | 0.570 | 2 | 1 | −0.053 |
| Average of the data of the 7 types | | 0.720 | | | | 0.684 | 2 | 1 | −0.036 |

The absolute values of the correlation coefficient of the operated value O, obtained by the subtraction type operation, that is, by the following formula (2), and the water potential are shown according to the measurement times in FIG. 7B. For each plant type, the measurement times for which the highest correlation coefficient value is obtained are shown together with the correlation coefficient value in Table 4.

$$O = D_{x1} - D_{x2} \quad (2)$$

TABLE 4

Correlation coefficient of the subtraction type index of the delayed luminescence amount and the water potential

| | Optimal times for each type | | | | Times that are optimal in average for the data of the 7 types | | | | Difference with respect to the optimal times for the data of each type Difference of the absolute values of the correlation coefficient |
|---|---|---|---|---|---|---|---|---|---|
| | Correlation coefficient | Absolute value | X1 (s) | X2 (s) | Correlation coefficient | Absolute value | X1 (s) | X2 (s) | |
| Camphor tree | 0.836 | 0.836 | 0.9 | 0.8 | 0.831 | 0.831 | 3 | 0.8 | −0.005 |
| Yoshino cherry | 0.750 | 0.750 | 300 | 1 | 0.719 | 0.719 | 3 | 0.8 | −0.031 |
| Japanese camellia | 0.675 | 0.675 | 5 | 4 | 0.644 | 0.644 | 3 | 0.8 | −0.032 |
| Kousa dogwood | 0.678 | 0.678 | 1 | 0.9 | 0.662 | 0.662 | 3 | 0.8 | −0.016 |
| Japanese mountain cherry | 0.661 | 0.661 | 5 | 1 | 0.647 | 0.647 | 3 | 0.8 | −0.014 |
| 2011 Japanese mountain cherry 2011 | 0.878 | 0.878 | 0.5 | 0.4 | 0.862 | 0.862 | 3 | 0.8 | −0.017 |
| Tomato | 0.668 | 0.668 | 60 | 0.5 | 0.666 | 0.666 | 3 | 0.8 | −0.002 |
| Average of the data of the 7 types | | 0.735 | | | | 0.719 | 3 | 0.8 | −0.017 |

The absolute values of the correlation coefficient of the operated value O, obtained by the normalized difference type operation, that is, by the following formula (3), and the water potential are shown according to the measurement time in FIG. 8. For each plant type, the measurement times for which the highest correlation coefficient value is obtained are shown together with the correlation coefficient value in Table 5.

$$O=(D_{x1}-D_{x2})/(D_{x1}+D_{x2}) \qquad (3)$$

of chlorophyll fluorescence and the water potential, which is the prior art, is 0.351 and is indicated in the figures by a thick line. In regard to the operation methods described above, it was found that all of the methods can provide a correlation coefficient higher than that in the case of using the Fv/Fm value of chlorophyll fluorescence as an index.

Values of the correlation coefficient of the delayed luminescence amount and the water potential at a single time are shown in Table 6.

TABLE 5

Correlation coefficient of the normalized difference type operation of the delayed luminescence amount and the water potential

| | Optimal times for each type | | | | Times that are optimal in average for the data of the 7 types | | | | Difference with respect to the optimal times for the data of each type Difference of the absolute values of the correlation coefficient |
|---|---|---|---|---|---|---|---|---|---|
| | Correlation coefficient | Absolute value | X1 (s) | X2 (s) | Correlation coefficient | Absolute value | X1 (s) | X2 (s) | |
| Camphor tree | 0.840 | 0.840 | 3 | 1 | 0.831 | 0.831 | 5 | 1 | −0.008 |
| Yoshino cherry | 0.539 | 0.539 | 5 | 1 | 0.539 | 0.539 | 5 | 1 | 0.000 |
| Japanese camellia | 0.828 | 0.828 | 7 | 0.1 | 0.736 | 0.736 | | 1 | −0.092 |
| Kousa dogwood | 0.674 | 0.674 | 2 | 0.9 | 0.661 | 0.661 | 5 | 1 | −0.013 |
| Japanese mountain cherry | 0.616 | 0.616 | 2 | 1 | 0.598 | 0.598 | 5 | 1 | −0.018 |
| 2011 Japanese mountain cherry 2011 | 0.891 | 0.891 | 1 | 0.4 | 0.865 | 0.865 | 5 | 1 | −0.026 |
| Tomato | 0.619 | 0.619 | 10 | 6 | 0.577 | 0.577 | 5 | 1 | −0.042 |
| Average of the data of the 7 types | | 0.715 | | | | 0.687 | 5 | 1 | −0.029 |

The absolute value (average value of the data of the seven plant types) of the correlation coefficient of the Fv/Fm value

TABLE 6

Correlation coefficient of the delayed luminescence amount and the water potential at a single time

| | Optimal times for each type | | | Times that are optimal in average for the data of the 7 types | | | Difference with respect to the optimal times for the data of each type Difference of the absolute values of the correlation coefficient |
|---|---|---|---|---|---|---|---|
| | Correlation coefficient | Absolute value | X (s) | Correlation coefficient | Absolute value | X (s) | |
| Camphor tree | −0.815 | 0.815 | 0.4 | −0.812 | 0.812 | 0.6 | −0.004 |
| Yoshino cherry | −0.756 | 0.756 | 1.4 | −0.724 | 0.724 | 0.6 | −0.032 |
| Japanese camellia | −0.662 | 0.662 | 0.2 | −0.649 | 0.649 | 0.6 | −0.012 |
| Kousa dogwood | −0.647 | 0.647 | 0.5 | −0.646 | 0.646 | 0.6 | −0.001 |

TABLE 6-continued

Correlation coefficient of the delayed luminescence amount
and the water potential at a single time

| | Optimal times for each type | | | Times that are optimal in average for the data of the 7 types | | | Difference with respect to the optimal times for the data of each type Difference of the absolute values of the correlation coefficient |
|---|---|---|---|---|---|---|---|
| | Correlation coefficient | Absolute value | X (s) | Correlation coefficient | Absolute value | X (s) | |
| Japanese mountain cherry 2011 | −0.653 | 0.653 | 1 | −0.642 | 0.642 | 0.6 | −0.012 |
| Japanese mountain cherry 2011 | −0.876 | 0.876 | 0.3 | −0.857 | 0.857 | 0.6 | −0.019 |
| Tomato | −0.668 | 0.668 | 0.5 | −0.668 | 0.668 | 0.6 | 0.000 |
| Average of the data of the 7 types | | 0.725 | | | 0.714 | 0.6 | −0.012 |

(Correlation Coefficients of Coefficient Values and the Water Potential)

The approximation formulae indicated below were obtained for data of the delayed luminescence amounts Y at measured times X in a fixed time period, and correlation coefficients of the coefficient values in each approximation formula and the water potential were calculated. FIGS. 9 to 12 show graphs showing the absolute values of the correlation coefficients of the various coefficients and the water potential according to the measurement time. Each of the values shown in the graphs is an average value of the data of the seven types of plants besides the potted Japanese mountain cherry.

The absolute values of the correlation coefficient of the coefficient a in the exponential function represented by the formula (4) and the water potential are shown according to the measurement times in FIG. 9A. For each plant type, the measurement times for which the highest correlation coefficient value is obtained are shown together with the correlation coefficient value in Table 7.

$$Y = a \cdot b^X \qquad (4)$$

TABLE 7

Correlation coefficient of the coefficient a of the exponential function and the water potential

| | Optimal times for each type | | | | Times that are optimal in average for the data of the 7 types | | | | Difference with respect to the optimal times for the data of each type Difference of the absolute values of the correlation coefficient |
|---|---|---|---|---|---|---|---|---|---|
| | Correlation coefficient | Absolute value | X1 (s) | X2 (s) | Correlation coefficient | Absolute value | X1 (s) | X2 (s) | |
| Camphor tree | −0.824 | 0.824 | 0.3 | 4 | −0.818 | 0.818 | 0.7 | 3 | −0.006 |
| Yoshino cherry | −0.752 | 0.752 | 4 | 6 | −0.723 | 0.723 | 0.7 | 3 | −0.029 |
| Japanese camellia | −0.643 | 0.643 | 0.2 | 8 | −0.641 | 0.641 | 0.7 | 3 | −0.002 |
| Kousa dogwood | −0.665 | 0.665 | 0.7 | 2 | −0.662 | 0.662 | 0.7 | 3 | −0.003 |
| Japanese mountain cherry | −0.676 | 0.676 | 3 | 4 | −0.651 | 0.651 | 0.7 | 3 | −0.025 |

TABLE 7-continued

Correlation coefficient of the coefficient a of the exponential function and the water potential

| | Optimal times for each type | | | | Times that are optimal in average for the data of the 7 types | | | | Difference with respect to the optimal times for the data of each type Difference of the absolute values of the correlation coefficient |
|---|---|---|---|---|---|---|---|---|---|
| | Correlation coefficient | Absolute value | X1 (s) | X2 (s) | Correlation coefficient | Absolute value | X1 (s) | X2 (s) | |
| 2011 Japanese mountain cherry 2011 | −0.881 | 0.881 | 0.3 | 2 | −0.853 | 0.853 | 0.7 | 3 | −0.028 |
| Tomato | −0.669 | 0.669 | 0.2 | 20 | −0.665 | 0.665 | 0.7 | 3 | −0.004 |
| Average of the data of the 7 types | | 0.730 | | | | 0.716 | 0.7 | 3 | −0.014 |

The absolute values of the correlation coefficient of the coefficient b in the exponential function represented by the formula (4) and the water potential are shown according to the measurement times in FIG. 9B. For each plant type, the measurement times for which the highest correlation coefficient value is obtained are shown together with the correlation coefficient value in Table 8.

TABLE 8

Correlation coefficient of the coefficient b of the exponential function and the water potential

| | Optimal times for each type | | | | Times that are optimal in average for the data of the 7 types | | | | Difference with respect to the optimal times for the data of each type Difference of the absolute values of the correlation coefficient |
|---|---|---|---|---|---|---|---|---|---|
| | Correlation coefficient | Absolute value | X1 (s) | X2 (s) | Correlation coefficient | Absolute value | X1 (s) | X2 (s) | |
| Camphor tree | 0.840 | 0.840 | 0.6 | 5 | 0.838 | 0.838 | 1 | 4 | −0.002 |
| Yoshino cherry | 0.541 | 0.541 | 2 | 6 | 0.533 | 0.533 | 1 | 4 | −0.009 |
| Japanese camellia | 0.818 | 0.818 | 0.1 | 1 | 0.714 | 0.714 | 1 | 4 | −0.104 |
| Kousa dogwood | 0.677 | 0.677 | 0.8 | 6 | 0.676 | 0.676 | 1 | 4 | −0.001 |
| Japanese mountain cherry | 0.612 | 0.612 | 1 | 2 | 0.607 | 0.607 | 1. | 4 | −0.005 |
| 2011 Japanese mountain cherry 2011 | 0.888 | 0.888 | 0.4 | 2 | 0.872 | 0.872 | 1 | 4 | −0.016 |
| Tomato | 0.624 | 0.624 | 0.5 | 30 | 0.569 | 0.569 | 1 | 4 | −0.055 |
| Average of the data of the 7 types | | 0.714 | | | | 0.687 | 1 | 4 | −0.027 |

Figure 10:
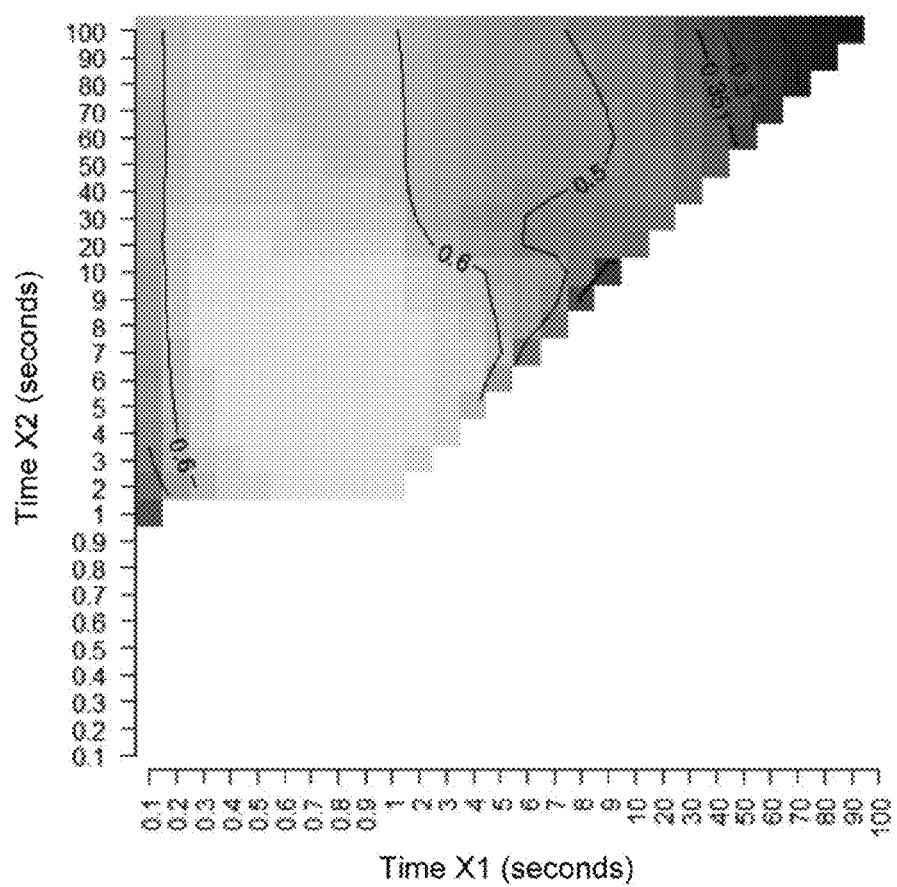
FIG. 10 is a graph of the absolute values of a correlation coefficient of a coefficient λ of an exponential function expressed by a formula (5) and the water potential in Example 1.
Figure 11:
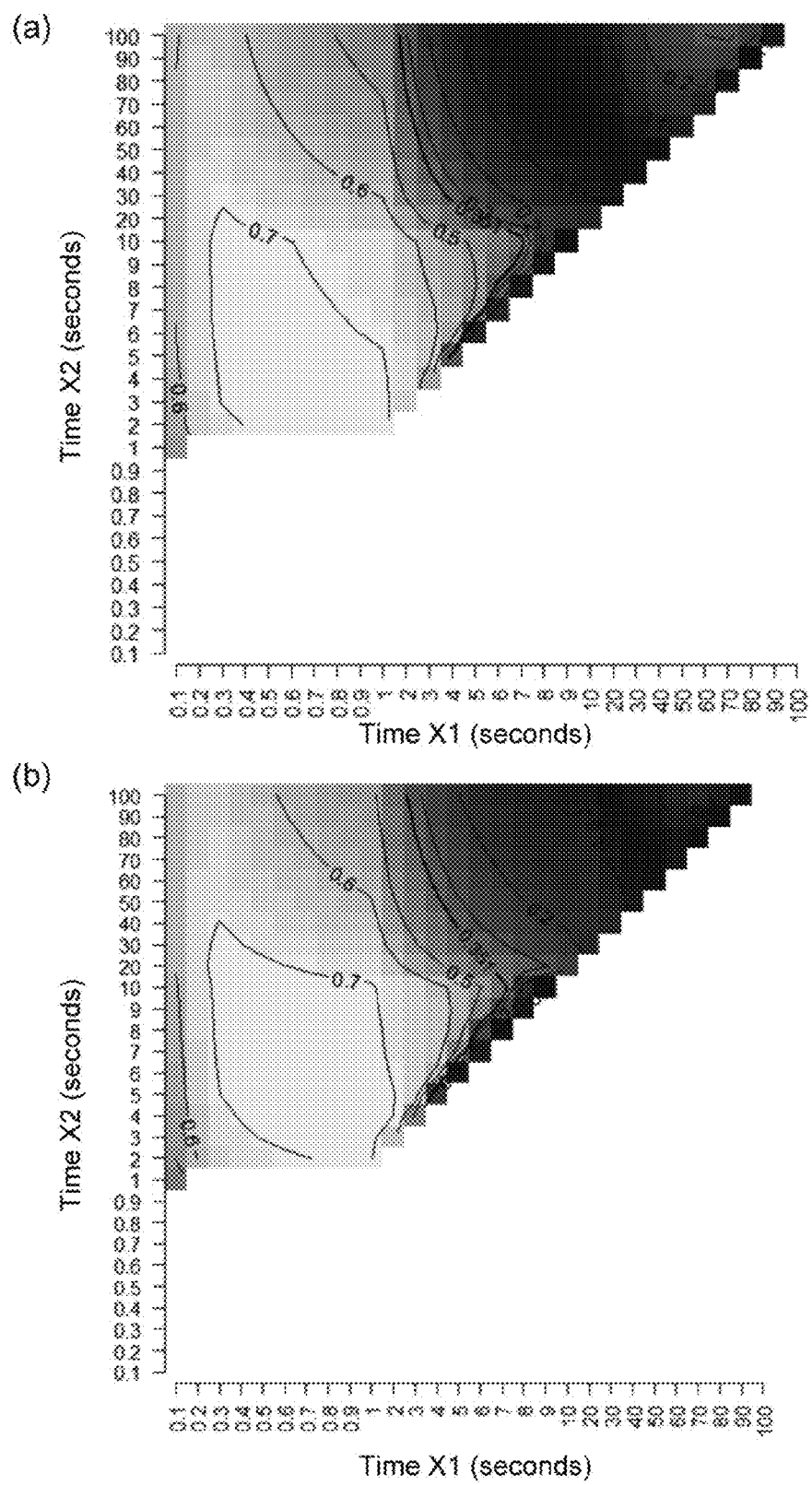
FIG. 11A is a graph of the absolute values of a correlation coefficient of a coefficient c of a quadratic function expressed by a formula (6) and the water potential in Example 1.
FIG. 11B is a graph of the absolute values of a correlation coefficient of a coefficient d of the quadratic function expressed by the formula (5) and the water potential in Example 1.

The absolute values of the correlation coefficient of the coefficient λ in the exponential function represented by the formula (5) and the water potential are shown according to the measurement times in FIG. 10. For each plant type, the measurement times for which the highest correlation coefficient value is obtained are shown together with the correlation coefficient value in Table 9.

$$Y = a \cdot e^{(-\lambda \cdot X)} \quad (5)$$

TABLE 9

Correlation coefficient of the coefficient λ of the exponential function and the water potential.

| | Optimal times for each type | | | | Times that are optimal in average for the data of the 7 types | | | | Difference with respect to the optimal times for the data of each type Difference of the absolute values of the correlation coefficient |
|---|---|---|---|---|---|---|---|---|---|
| | Correlation coefficient | Absolute value | X1 (s) | X2 (s) | Correlation coefficient | Absolute value | X1 (s) | X2 (s) | |
| Camphor tree | −0.843 | 0.843 | 0.6 | 5 | −0.842 | 0.842 | 1 | 4 | −0.002 |
| Yoshino cherry | −0.543 | 0.543 | 2 | 6 | −0.534 | 0.534 | 1 | 4 | −0.009 |
| Japanese camellia | −0.759 | 0.759 | 0.1 | 1 | −0.691 | 0.691 | 1 | 4 | −0.068 |
| Kousa dogwood | −0.680 | 0.680 | 0.9 | 6 | −0.679 | 0.679 | 1 | 4 | 0.000 |
| Japanese mountain cherry | −0.614 | 0.614 | 1 | 2 | −0.609 | 0.609 | 1 | 4 | −0.005 |
| 2011 Japanese mountain cherry 2011 | −0.892 | 0.892 | 0.4 | 2 | −0.875 | 0.875 | 1 | 4 | −0.017 |
| Tomato | −0.623 | 0.623 | 0.6 | 30 | −0.568 | 0.568 | 1 | 4 | −0.055 |
| Average of the data of the 7 types | | 0.708 | | | | 0.685 | 1 | 4 | −0.022 |

The absolute values of the correlation coefficient of the coefficient c in the quadratic function represented by the formula (6) and the water potential are shown according to the measurement times in FIG. 11A. For each plant type, the measurement times for which the highest correlation coefficient value is obtained are shown together with the correlation coefficient value in Table 10.

$$Y = c + d \cdot X + e \cdot X^2 \tag{6}$$

TABLE 10

Correlation coefficient of the coefficient c of the quadratic function and the water potential

| | Optimal times for each type | | | | Times that are optimal in average for the data of the 7 types | | | | Difference with respect to the optimal times for the data of each type Difference of the absolute values of the correlation coefficient |
|---|---|---|---|---|---|---|---|---|---|
| | Correlation coefficient | Absolute value | X1 (s) | X2 (s) | Correlation coefficient | Absolute value | X1 (s) | X2 (s) | |
| Camphor tree | −0.821 | 0.821 | 0.3 | 4 | −0.817 | 0.817 | 0.7 | 3 | −0.005 |
| Yoshino cherry | −0.754 | 0.754 | 1 | 10 | −0.724 | 0.724 | 0.7 | 3 | −0.030 |
| Japanese camellia | −0.659 | 0.659 | 0.2 | 10 | −0.648 | 0.648 | 0.7 | 3 | −0.011 |
| Kousa dogwood | −0.656 | 0.656 | 0.7 | 2 | −0.652 | 0.652 | 0.7 | 3 | −0.004 |
| Japanese mountain cherry | −0.666 | 0.666 | 3 | 5 | −0.648 | 0.648 | 0.7 | 3 | −0.018 |
| 2011 Japanese mountain cherry 2011 | −0.885 | 0.885 | 0.3 | 2 | −0.856 | 0.856 | 0.7 | 3 | −0.029 |

TABLE 10-continued

Correlation coefficient of the coefficient c of the quadratic function and the water potential

|  | Optimal times for each type | | | | Times that are optimal in average for the data of the 7 types | | | | Difference with respect to the optimal times for the data of each type Difference of the absolute values of the correlation coefficient |
| --- | --- | --- | --- | --- | --- | --- | --- | --- | --- |
|  | Correlation coefficient | Absolute value | X1 (s) | X2 (s) | Correlation coefficient | Absolute value | X1 (s) | X2 (s) |  |
| Tomato | −0.670 | 0.670 | 0.2 | 10 | −0.664 | 0.664 | 0.7 | 3 | −0.006 |
| Average of the data of the 7 types |  | 0.730 |  |  |  | 0.716 | 0.7 | 3 | −0.015 |

The absolute values of the correlation coefficient of the coefficient d in the quadratic function represented by the formula (6) and the water potential are shown according to the measurement times in FIG. 11B. For each plant type, the measurement times for which the highest correlation coefficient value is obtained are shown together with the correlation coefficient value in Table 11.

Figure 12:
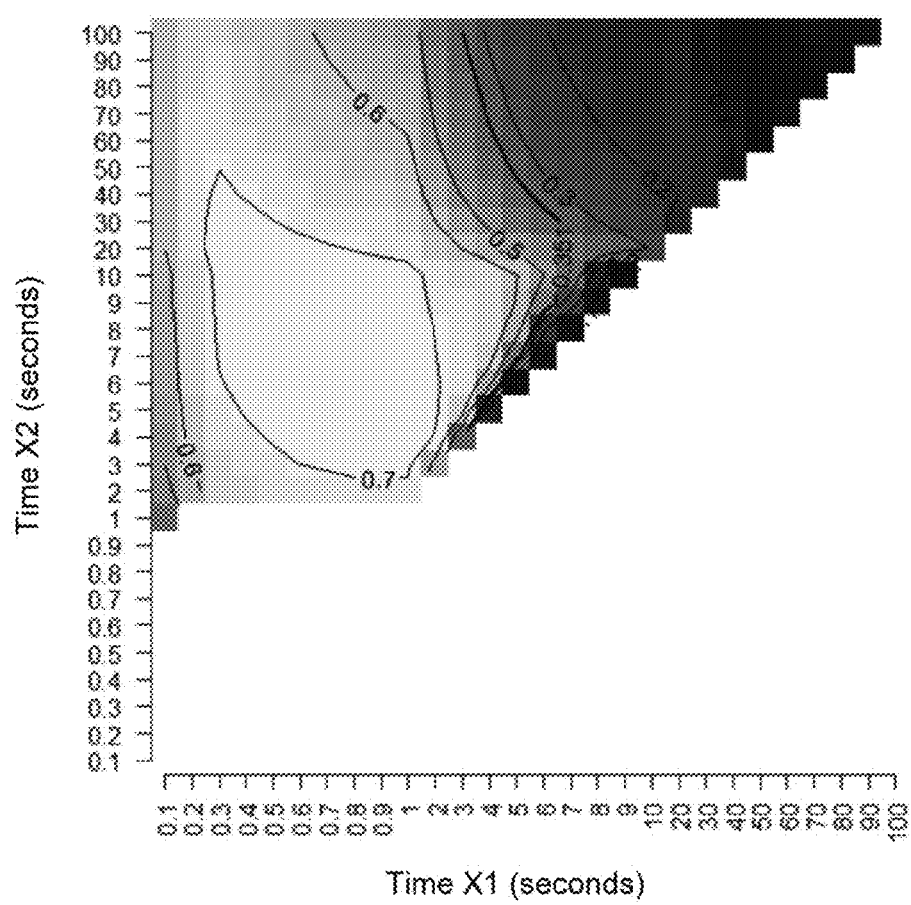
FIG. 12 is a graph of the absolute values of a correlation coefficient of a coefficient e of the quadratic function expressed by the formula (6) and the water potential in Example 1.

The absolute values of the correlation coefficient of the coefficient e in the quadratic function represented by the formula (6) and the water potential are shown according to the measurement times in FIG. 12. For each plant type, the measurement times for which the highest correlation coefficient value is obtained are shown together with the correlation coefficient value in Table 12.

TABLE 11

Correlation coefficient of the coefficient d of the quadratic function and the water potential

|  | Optimal times for each type | | | | Times that are optimal in average for the data of the 7 types | | | | Difference with respect to the optimal times for the data of each type Difference of the absolute values of the correlation coefficient |
| --- | --- | --- | --- | --- | --- | --- | --- | --- | --- |
|  | Correlation coefficient | Absolute value | X1 (s) | X2 (s) | Correlation coefficient | Absolute value | X1 (s) | X2 (s) |  |
| Camphor tree | 0.832 | 0.832 | 0.8 | 4 | 0.830 | 0.830 | 0.8 | 5 | −0.002 |
| Yoshino cherry | 0.752 | 0.752 | 0.7 | 30 | 0.718 | 0.718 | 0.8 | 5 | −0.034 |
| Japanese camellia | 0.662 | 0.662 | 0.2 | 20 | 0.644 | 0.644 | 0.8 | 5 | −0.018 |
| Kousa dogwood | 0.669 | 0.669 | 0.8 | 3 | 0.664 | 0.664 | 0.8 | 5 | −0.004 |
| Japanese mountain cherry 2011 | 0.690 | 0.690 | 3 | 5 | 0.655 | 0.655 | 0.8 | 5 | −0.035 |
| Japanese mountain cherry 2011 | 0.885 | 0.885 | 0.3 | 3 | 0.861 | 0.861 | 0.8 | 5 | −0.024 |
| Tomato | 0.667 | 0.667 | 0.2 | 20 | 0.661 | 0.661 | 0.8 | 5 | −0.006 |
| Average of the data of the 7 types |  | 0.737 |  |  |  | 0.719 | 0.8 | 5 | −0.018 |

TABLE 12

Correlation coefficient of the coefficient e of the quadratic function and the water potential

| | Optimal times for each type | | | | Times that are optimal in average for the data of the 7 types | | | | Difference with respect to the optimal times for the data of each type Difference of the absolute values of the correlation coefficient |
|---|---|---|---|---|---|---|---|---|---|
| | Correlation coefficient | Absolute value | X1 (s) | X2 (s) | Correlation coefficient | Absolute value | X1 (s) | X2 (s) | |
| Camphor tree | −0.836 | 0.836 | 1 | 4 | −0.835 | 0.835 | 1 | 5 | −0.001 |
| Yoshino cherry | −0.751 | 0.751 | 0.6 | 40 | −0.716 | 0.716 | 1 | 5 | −0.036 |
| Japanese camellia | −0.664 | 0.664 | 0.2 | 30 | −0.640 | 0.640 | 1 | 5 | −0.024 |
| Kousa dogwood | −0.671 | 0.671 | 0.8 | 5 | −0.668 | 0.668 | 1 | 5 | −0.004 |
| Japanese mountain cherry | −0.697 | 0.697 | 3 | 6 | −0.659 | 0.659 | 1 | 5 | −0.038 |
| 2011 Japanese mountain cherry 2011 | −0.885 | 0.885 | 0.3 | 5 | −0.862 | 0.862 | 1 | 5 | −0.023 |
| Tomato | −0.666 | 0.666 | 0.2 | 30 | −0.658 | 0.658 | 1 | 5 | −0.009 |
| Average of the data of the 7 types | | 0.739 | | | | 0.720 | 1 | 5 | −0.019 |

For the five species of camphor tree, Japanese camellia, Kousa dogwood, Japanese mountain cherry, and tomato, the operated value obtained by the subtraction type operation among the abovementioned operation methods was the highest in correlation with the water potential (vitality index reflecting acute stress) and was the best as an index value for vitality evaluation. With Yoshino cherry, the method using the delayed luminescence amount data at one point in time within the time domain A as the index value, which is the evaluation method according to the first embodiment, exhibited the highest correlation with the water potential. Therefore in the evaluation system, evaluation of higher accuracy can be performed, for example, by using the subtraction type operated value as the optimal index value for evaluation of the abovementioned five species of plants and using the delayed luminescence amount data for Yoshino cherry.

Example 2

Measurements in the Field (Japanese Mountain Cherry)

Figure 4:
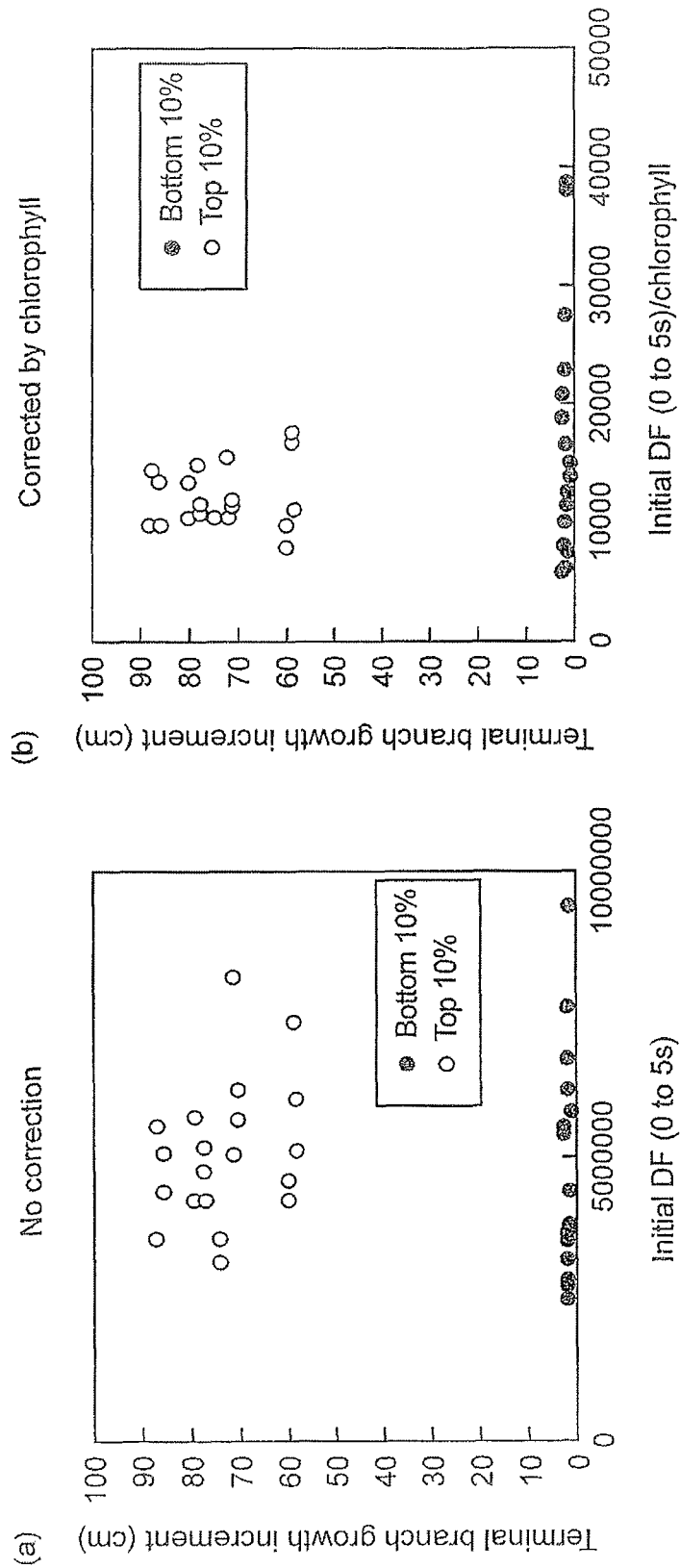
FIG. 4 shows plot diagrams of a relationship of terminal branch growth increment and delayed luminescence amount from 0 to 5 seconds after start of measurement (immediately after end of irradiation of excitation light) in Example 2.

Terminal branches at treetop portions of Japanese mountain cherry (*Cerasus jamasakura* var. *jamasakura*) growing in the field (outdoors) were collected and carried to a measurement location while being careful not to apply damage, and measurements were performed in accordance with the following protocol. With each terminal branch that was carried, the branch growth increment was measured, two leaves that were representative in appearance among the leaves of the terminal branch were selected, and measurement of weak luminescence was performed immediately on the two leaves. With the exception of the measurement time being 300 seconds, the measurements of the weak luminescence were performed with the other conditions being the same as those of Example 1. Here, the terminal branch growth increment is the amount of elongation of a branch of the current year from the beginning of spring of that year to the time of measurement and is an index that expresses the growth state of the subject plant and is also a vitality index that reflects chronic stress. FIG. 4 shows the terminal branch growth increments and the (cumulative) delayed luminescence amounts in an interval of 0 to 5 seconds from the start of measurement (immediately after the end of excitation light irradiation) of a bottom 10% group of short terminal branch increment and a top 10% group of long terminal branch increment among a total of 204 leaves collected from 102 individual trees.

FIG. 4A is a plot diagram of a relationship of the terminal branch growth increment and the delayed luminescence amount of the top 10% group and the bottom 10% group. FIG. 4B is a plot diagram of a relationship of the terminal branch growth increment and a corrected delayed luminescence amount (values obtained by dividing the respective delayed luminescence amounts by the respective chlorophyll amounts). Although in the case where correction by the chlorophyll amount is not performed, there is not much difference in delayed luminescence amount between the bottom 10% and the top 10%, when the correction by the chlorophyll amount is performed, the delayed luminescence amount became higher than those of the top 10% in a portion of the bottom 10%.

A change with time of a correlation coefficient of the terminal branch growth increment and the delayed luminescence amount from immediately after excitation light irradiation in Example 2 is shown in FIG. 5. The correlation coefficient took a maximum value of 0.488 at 30 seconds after excitation light irradiation. From the results of Example 2, it is considered that the delayed luminescence amount at several dozen seconds after excitation light irradiation is related to the terminal branch growth increment that is a growth index of a longer term (vitality index reflecting chronic stress).

Figure 6:
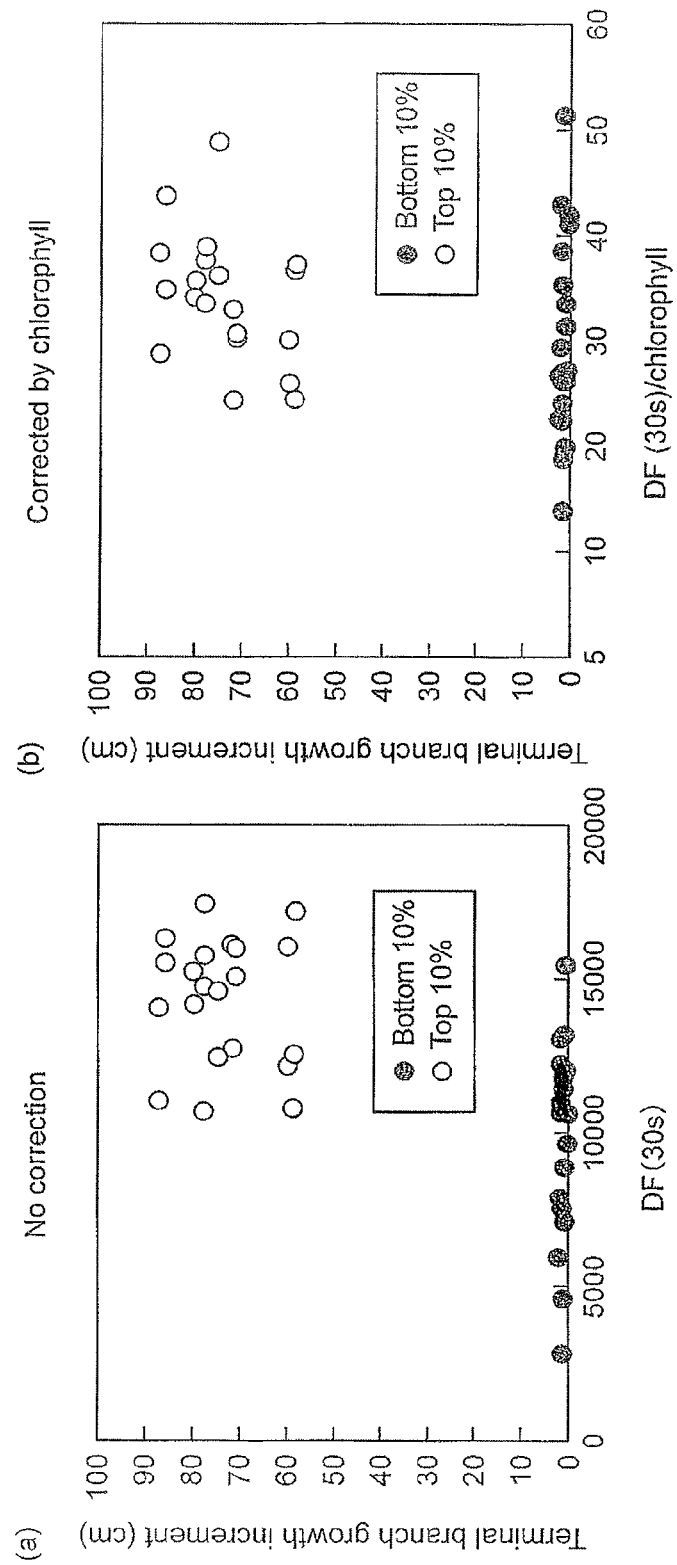
FIG. 6 shows plot diagrams of a relationship of terminal branch growth increment and delayed luminescence amount at 30 seconds after start of measurement (immediately after end of irradiation of excitation light) in Example 2.

FIG. 6 shows the terminal branch growth increments and the delayed luminescence amounts at 30 seconds from the start of measurement for the bottom 10% group of having short terminal branch increment and top 10% group of having long terminal branch increment among the total of 204 leaves identical those of Example 2 collected from 102 individual trees.

FIG. 6A is a plot diagram of a relationship of the terminal branch growth increment and the delayed luminescence amount of the top 10% group and the bottom 10% group. FIG. 6B is a plot diagram of a relationship of the terminal branch growth increment and the corrected delayed luminescence amount (values obtained by dividing the respective delayed luminescence amounts by the respective chlorophyll amounts). With the delayed luminescence amount at 30 seconds after excitation light irradiation, the plots of the group of long terminal branch growth increment (top 10%) and the group of short terminal branch growth increment (bottom 10%) were separated even without the correction by the chlorophyll amount. In the evaluation of chronic stress, the effect of correction by the chlorophyll amount was not seen in particular.

DESCRIPTION OF THE SYMBOL(S)

10 . . . shutter opening, 15 . . . shutter, 20 . . . main body portion, 21 . . . end portion, 30, 31, 32 . . . jig, 50 . . . light collecting unit, 55 . . . lens, 60 . . . light source unit 70 . . . optical fiber or relay optical system, 80 . . . delayed luminescence detecting unit, 81 . . . shutter, 82 . . . condenser lens, 83 . . . display unit, 84 . . . input unit, 85 . . . photodetector, 100 . . . dark treatment tool, 200 . . . measurement apparatus, 300 . . . vitality evaluation system

What is claimed is:

1. A method for evaluating vitality of a plant in management of roadside trees, park trees, and garden trees, and in production of agricultural plants, comprising:
   measuring delayed luminescence amounts of a leaf of a plant subject to evaluation at x seconds and y seconds after excitation light irradiation, where x and y are x≠y, to obtain two data items $D_{x1}$ and $D_{x2}$ of delayed luminescence amount, wherein the delayed luminescence amounts are measured noninvasively, wherein x and y are 0.8 to 5 when the evaluating vitality is based on a vitality index that reflects acute stress, and x and y are 10 to 300 when the evaluating vitality is based on a vitality index that reflects chronic stress, wherein the vitality index that reflects acute stress is a sudden variation of water potential or xylem pressure potential, and wherein the vitality index that reflects chronic stress is a decrease of branch growth increment and/or trunk growth increment, and wherein the plant is selected from the group consisting of a roadside tree, a park tree, a garden tree, and an agricultural plant;
   obtaining an operated value by any of the following formulae (1), (2), and (3) using $D_{x1}$ and $D_{x2}$:

$$O=D_{x1}/D_{x2} \qquad (1)$$

$$O=D_{x1}-D_{x2} \qquad (2)$$

$$O=(D_{x1}-D_{x2})/(D_{x1}+D_{x2}) \qquad (3)$$

wherein $D_{x1}$ represents the data item of delayed luminescence amount at x seconds after excitation light irradiation, $D_{x2}$ represents the data item of delayed luminescence amount at y seconds after excitation light irradiation, and O represents the operated value, wherein the data is processed by any of the following (i), (ii), and (iii):
   (i) ranking the data items based on the obtained operated value or a coefficient value;
   (ii) assuming a normal distribution to calculate a prediction interval corresponding to the preset upper limit threshold or the preset lower limit threshold, and classifying the data items based on the prediction interval; and
   (iii) calculating, by a bootstrap method, a confidence interval of percentile value corresponding to the preset upper limit threshold or the preset lower limit threshold, and classifying the data items based on the confidence interval;
   comparing the obtained operated value with a predetermined threshold;
   determining a vitality state of the plant based upon the comparison of the operated value with the predetermined threshold,
   wherein an individual plant having the operated value not less than a preset upper limit threshold is determined as an individual of good growth, and/or an individual plant having the operated value not more than a preset lower limit threshold is determined as an individual of poor growth, if the vitality index correlates positively with the operated value, and
   wherein the individual plant having the operated value not less than the preset upper limit threshold is determined as the individual of poor growth, and/or the individual plant having the operated value not more than a preset lower limit threshold is determined as the individual of good growth, if the vitality index correlates negatively with the operated value; and
   identifying and selecting the plant that is determined as an individual of good growth or poor growth.

2. The method for evaluating vitality according to claim 1, wherein x and y are included in a time domain of 0.2 to 300 seconds after excitation light irradiation.

3. The method for evaluating vitality according to claim 1, further comprising:
   measuring a chlorophyll amount in the plant leaf to obtain chlorophyll amount data; and
   calculating data of corrected delayed luminescence amount by correcting the obtained data of delayed luminescence amount by the chlorophyll amount per predetermined area;
   wherein the data items of corrected delayed luminescence amount are used in place of the data items of delayed luminescence amount in the obtaining of the operated value or the coefficient value.

* * * * *